US012575787B2

(12) United States Patent
Weiss

(10) Patent No.: US 12,575,787 B2
(45) Date of Patent: Mar. 17, 2026

(54) APPARATUS AND METHOD FOR THE DETECTION OF DEMENTIA AND RETINAL CONDITIONS

(71) Applicant: Jeffrey N. Weiss, Parkland, FL (US)

(72) Inventor: Jeffrey N. Weiss, Parkland, FL (US)

( * ) Notice: Subject to any disclaimer, the term of this patent is extended or adjusted under 35 U.S.C. 154(b) by 0 days.

(21) Appl. No.: 19/030,596

(22) Filed: Jan. 17, 2025

(65) Prior Publication Data

US 2025/0160739 A1 May 22, 2025

Related U.S. Application Data

(63) Continuation of application No. 18/129,202, filed on Mar. 31, 2023, now Pat. No. 12,207,940, which is a continuation-in-part of application No. 17/724,324, filed on Apr. 19, 2022, now Pat. No. 11,666,213, which is a continuation-in-part of application No. 16/257,518, filed on Jan. 25, 2019, now abandoned.

(60) Provisional application No. 62/622,775, filed on Jan. 26, 2018.

(51) Int. Cl.
| | |
|---|---|
| *A61B 5/00* | (2006.01) |
| *A61B 3/00* | (2006.01) |
| *A61B 3/10* | (2006.01) |

(52) U.S. Cl.
CPC .......... *A61B 5/4848* (2013.01); *A61B 3/0008* (2013.01); *A61B 3/102* (2013.01); *A61B 5/4088* (2013.01); *A61B 5/7246* (2013.01); *A61B 5/7275* (2013.01)

(58) Field of Classification Search
CPC ..... A61B 5/4848; A61B 3/0008; A61B 3/102; A61B 5/4088; A61B 5/7246; A61B 5/7275; A61B 3/10; A61B 5/6803; A61B 5/4047; A61B 2562/0233; A61B 2562/223; A61B 2562/228; A61B 3/12; A61B 5/0066
USPC ........................................................ 600/300
See application file for complete search history.

(56) References Cited

U.S. PATENT DOCUMENTS

| | | | |
|---|---|---|---|
| 11,666,213 B1 * | 6/2023 | Weiss ................... | A61B 5/4848 |
| | | | 600/425 |
| 12,207,940 B1 * | 1/2025 | Weiss ................... | A61B 5/6803 |
| 2003/0009156 A1 * | 1/2003 | Levine ................... | A61B 3/103 |
| | | | 606/5 |

(Continued)

*Primary Examiner* — Mohammed A Hasan
(74) *Attorney, Agent, or Firm* — Daniel S. Polley, PA

(57) ABSTRACT

An apparatus and method for aiding in the detection of dementia, concussion, other neurologic conditions, retinal, and optic nerve conditions. The apparatus enables the diffusion coefficient of the tissue to be ascertained and studied by directing the light from a laser or other coherent light source at the patient's retina, optic nerve or choroid and measuring the fluctuations in the intensity of the backscattered light caused by the movement of light scatterers in the tissue. By comparing the measurements to a normal database, or to the subject's previous measurement, in combination with an eye examination and OCT image/measurement the changes caused by the disease and the effectiveness of therapy can be ascertained. The disclosed apparatus allows the incident and detection optics to be attached to ophthalmic devices typically used in ophthalmologic care. Also, where both the incident laser fiber optic and the detection fiber optic are directly connected to goggles, one or more or all of the above-described mirrors may not be necessary, as both fiber optics are preferably directly directed into the eye.

18 Claims, 17 Drawing Sheets

EYEGLASSES

LENS

DETECTION FIBER

INCIDENT (LASER) FIBEROPTIC

(56)           References Cited

U.S. PATENT DOCUMENTS

| | | | |
|---|---|---|---|
| 2008/0151256 A1* | 6/2008 | Kikawa | G01B 9/02068 |
| | | | 356/498 |
| 2010/0142780 A1* | 6/2010 | Yasuno | G01N 21/4795 |
| | | | 382/131 |
| 2010/0157311 A1* | 6/2010 | Hayashi | A61B 3/1025 |
| | | | 356/496 |
| 2016/0278635 A1* | 9/2016 | Fukuma | A61B 3/0025 |
| 2021/0267801 A1* | 9/2021 | Akiyama | G16H 30/40 |
| 2024/0108212 A1* | 4/2024 | Leahy | A61B 3/12 |

* cited by examiner

| Item | Supplier | Part |
|---|---|---|
| Launching lens | Thorlabs | PAFA-X-4-A |
| 96:4 Fibered beam splitter | OZ Optics | FOBS-12N-111-4/125-PPP-633-96/4-40-3A3A3A-1-1 |
| Photon correlation module input to photon counting module parch cord | OZ Optics | PMJ-3A3A-633-4/125-3-1-1 |
| Laser output to collimator 1 (emission) | OZ Optics | PMJ-3A3A-633-4/125-3-3-1 |
| Collimator 2 to photon correlation module input | OZ Optics | PMJ-3A3A-633-4/125-3-3-1 |
| Collimator 1 | Thorlabs | PAF-X-5-B |
| Collimator 2 | Thorlabs | PAF-X-5-B |

Note: Optical fibers have a cladding and a core diameter of 124 and 4 μm respectively, and a numerical aperture of 0.11. They are polarization-maintaining to avoid polarization-related laser power fluctuations. All fiber optic connectors are FC-APC narrow key types.

Table 1. Fiber optics components

FIG. 4

APPARATUS AND METHOD FOR THE DETECTION OF
DEMENTIA AND RETINAL CONDITIONS
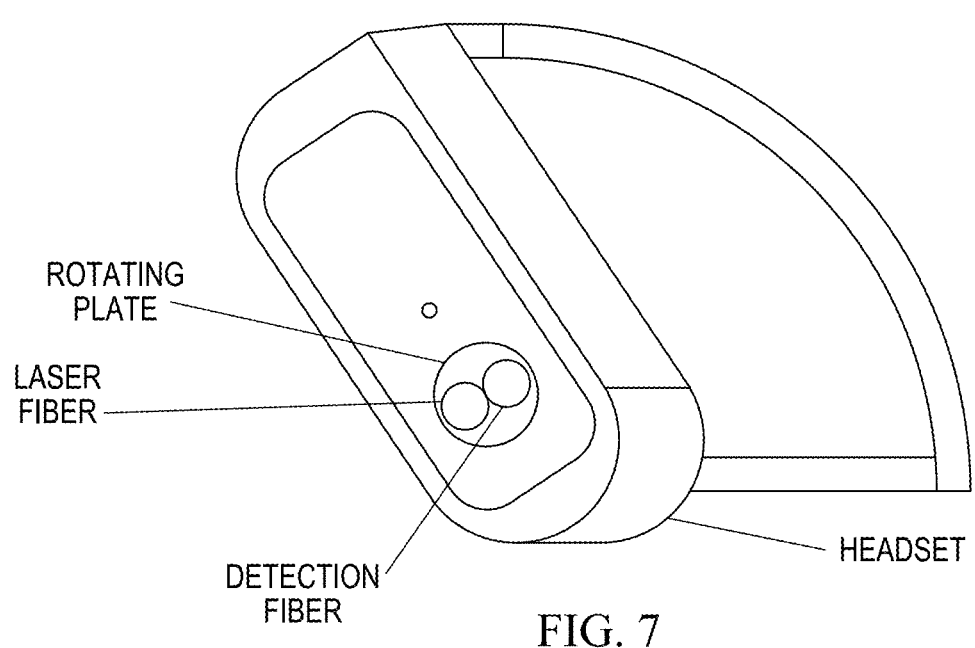
FIG. 7
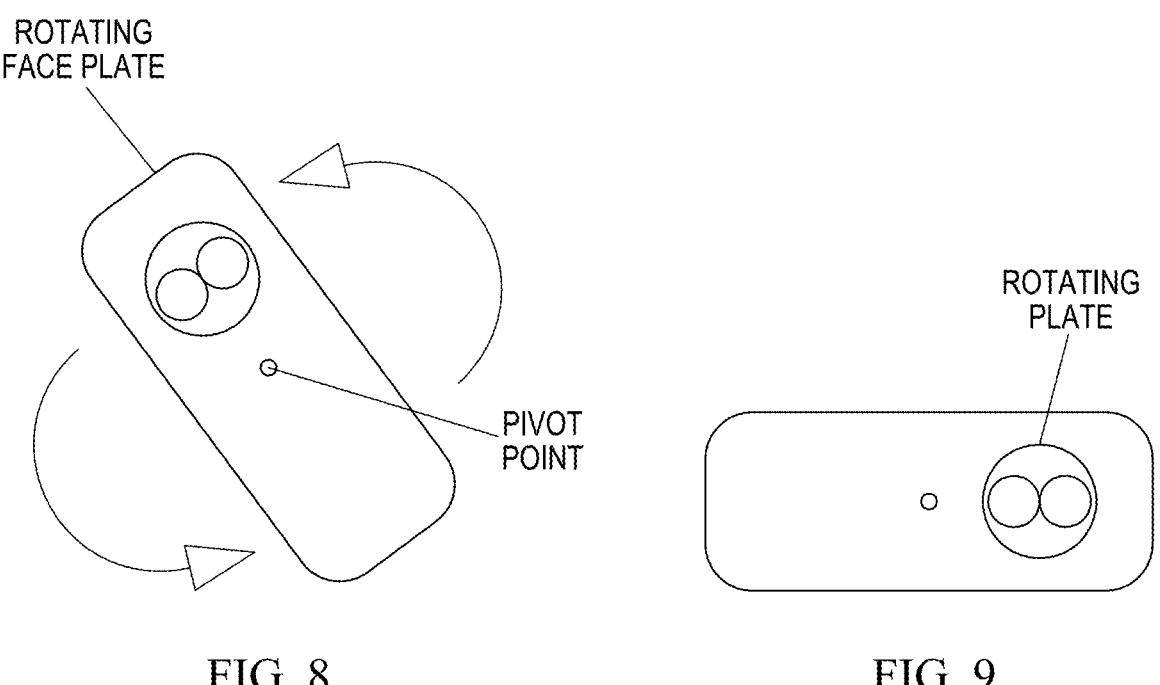
FIG. 8
FIG. 9

GROSS
FOCUS

ADJUSTMENT SCREW
FOR FINE FOCUS

ROTATING
FACE PLATE

MALLEABLE
RUBBER

HOLES FOR FIBEROPTIC
CONNECTORS

ROTATING
FACE PLATE

PROTECTIVE CAP OVER
FIBEROPTIC CONNECTOR

FIBEROPTIC CABLE CONTAINING BOTH
INCIDENT (LASER) FIBEROPTIC AND DETECTION FIBEROPTIC

CONNECTS TO LASER
AND DETECTION DEVICES

FIBEROPTIC CABLE CONNECTS
TO EITHER EYE LENS

APPARATUS AND METHOD FOR THE DETECTION OF DEMENTIA AND RETINAL CONDITIONS

This application is a continuation of U.S. application Ser. No. 18/129,202, filed Mar. 31, 2023, which is a continuation-in-part of U.S. application Ser. No. 17/724,324, filed Apr. 19, 2022, which is a continuation-in-part of U.S. application Ser. No. 16/257,518, file Jan. 25, 2019, which application claims priority to and the benefit of U.S. Application Ser. No. 62/622,775, filed Jan. 26, 2018. All of the above-identified applications are incorporated by reference in their entireties for all purposes.

This application also incorporates by reference U.S. Application Ser. No. 61/475,030, filed Apr. 13, 2011 in its entirety for all purposes.

FIELD OF THE INVENTION

This invention relates to medical diagnostic and monitoring methods and, in particular, to a method for the detection and monitoring of dementia and the effectiveness of potential therapies.

BACKGROUND OF THE INVENTION

Dementia is a common cause of morbidity and mortality. It is caused by physical changes in the brain that causes the loss of mental abilities and memory that affect the activities of daily living. The types of dementia include: Alzheimer's disease, Vascular dementia, Dementia with Lewy bodies, Mixed dementia, Parkinson's disease, Frontotemporal dementia, Creutzfeld-Jakob disease, Normal pressure hydrocephalus, Huntington's disease, Wernicke-Korsakoff Syndrome, etc.

Alzheimer's disease is a slowly progressive brain disease beginning prior to the appearance of symptoms and accounts for approximately 60-80% of dementia cases. Definitive diagnosis is made posthumously with the discovery of protein fragment beta-amyloid plaques and twisted strands of the protein tau (tangles) with nerve cell damage and death.

Vascular dementia, previously known as post-stroke or multi-infarct dementia is solely diagnosed in approximately 10% of dementia cases. The development of Lewy bodies in the cerebral cortex can cause dementia. The type of aggregate pattern may be indicative of Dementia with Lewy bodies or of Parkinson's disease.

Abnormalities of more than one dementia cause may occur simultaneously in the brain causing a mixed dementia. In Parkinson's disease the alpha-synuclein clumps generally occur in a deep area of the brain called the substantia nigra and are thought to affect the production of dopamine.

In Normal Pressure Hydrocephalus an abnormal increase of fluid in the brain leads to dementia. This may sometimes be corrected by the placement of a shunt in the brain to drain the excess fluid. There are no definite distinguishing microscopic abnormalities seen in all cases of frontotemporal dementia.

Creutzfeldt-Jakob disease (mad-cow disease) is caused by an infection with a prion. Huntington's disease is caused by a defective gene on chromosome 4. Vitamin B-1 deficiency (thiamine), generally caused by alcoholism, is the cause of Wernicke-Korsakoff syndrome.

In the absence of dementia etiology, as seen in Creutzfeldt-Jakob disease, Normal Pressure Hydrocephalus, Huntington's disease, Wernicke-Korsakoff syndrome, the true diagnosis is generally made pathologically, after the patient has expired.

During the last 15 years there have been more than 400 clinical trials of therapeutic agents for Alzheimer's disease registered with the National Institute of Health website, clinicaltrials.gov. For those trials with reported results, the failure rate has been almost 100%. Though most trials typically last 1.5 to 3 years, it has been estimated that, depending on the efficacy of the therapeutic intervention, study duration would need to be 5-10 years in duration to detect an effect.

Therefore, what is needed is a sensitive, quantitative, technique that can detect the beginnings or early onset of these conditions before the development of symptoms.

The retina is visible within the eye and is composed of 10 histologic layers. The nerve fiber layer of the retina is an extension of the brain. The early detection of neurologic damage at the microscopic level when it is still potentially reversible is a prerequisite for the development of potential cures. The early detection of the effectiveness of treatment allows for better and more effective treatments.

It has been demonstrated that patients with Alzheimer's disease have thinning of the retinal nerve fiber layer and retinal ganglion cell layer by ocular coherence tomography (OCT) images and measurements taken through the macula and peripapillary areas. This was consistent with histopathologic data. Inner retinal thinning has been correlated with disease severity. This may be related to the presence of amyloid-beta within the retina.

Inner retinal thinning has been found in other neurodegenerative diseases including multiple sclerosis, amyotrophic lateral sclerosis, dementia with Lewy bodies, and multiple system atrophy.

As compared to the inner retinal thinning seen in Alzheimer's disease, thinning of the photoreceptor or outer retina thinning has been found in frontotemporal degeneration. Approximately 30% of patients initially diagnosed with frontotemporal degeneration are subsequently diagnosed with Alzheimer's disease at autopsy.

Dynamic Light Scattering, also known as Photon Correlation Spectroscopy (PCS), a technique which measures the scattered light intensity fluctuations resulting from the thermal random motion (Brownian motion), has been used to predict the development of cataractogenesis in rabbits, and detect the development of cataract formation and of diabetes mellitus in humans. The results demonstrated the utility of PCS to noninvasively quantitate subtle changes at the molecular level.

The present disclosure is directed to addressing the need for a sensitive, quantitative technique that can detect the beginnings or early onset of the below listed conditions before the development of symptoms.

1. Light Scattering

Light is a type of electromagnetic energy emitted by sources, propagated through space, and absorbed and reflected by matter. In 1801, Thomas Young developed the wave model of light. When a light wave is absorbed the wave function collapses. The light is called a photon and represents a quanta of light. Light exhibits a wave-particle duality. When light travels, there is an electric and a magnetic field and both rapidly oscillate at approximately $10^{14}$ cycles/see around zero. When a light beam hits a particle the electric field of the light beam exerts an oscillating force on the nuclei and the electrons of the particle. While the heavier nuclei remain essentially unaffected, the lighter electrons undergo an oscillating acceleration radiating electromagnetic fields into space. The light wave energy accelerates electrons and this energy is transferred to the particle such that light travels in all directions. The incident beam loses power. An observer can see the scattered light. If there was no scattering, to the observer the light beam would appear to be invisible. The power of the scattering medium is expressed as turbidity as it attenuates the passing light. This may be expressed as:

$$-dI = \tau I\, dz \qquad (1)$$

Where:
z=light beam moving in a particular direction
I=light intensity at a particular position
−dI=light intensity lost
$\tau$=constant dependent on number of scattering particles, size, and polarizability or electron density in cm$^{-1}$
This equation applies to a thin portion of the scattering medium. Integrating Equation (1) describes the effect along the entire length of the medium.

$$\frac{I}{Io} = e^{-rz} \qquad (2)$$

Where:
$I_o$=intensity of primary beam at z=zero
I=intensity of primary beam after traversing distance z
e=natural base of logarithms
Using the normal human cornea as an example, there is an approximately 10 percent loss of the primary or incident light beam traversing the cornea. If we assume the normal corneal thickness, z=0.05 cm then I/$I_o$≈0.90 from Equation 2. Turbidity characterizes the quality of transparency of a scattering medium. It is apparent that the degree of turbidity is related to the microscopic tissue structure. With respect to turbidity relating to particle density, particle shape and size will affect its ability to scatter light. There is also a dependency of particle size as related to the wavelength of incident light. If we assume that each particle is an independent scatterer then:

$$dI = n\,\alpha\, I\, dz \qquad (3)$$

Where:
I=incident light intensity (ergs/see cm$^2$)
$\alpha$=proportionality coefficient (light scattering effectiveness)
dz=distance traveled by light
n=number of scattering particles/unit volume Integrading Equation (3): $\tau = na$ $\tau$=constant dependent on number of scattering particles, size, and polarizability or electron density in cm$^{-1}$ (turbidity)
n=number of scattering particles/unit volume
$\alpha$=proportionality coefficient (light scattering effectiveness)
Conceptually, the turbidity increases in proportion to the density. However, this assumes independent scattering, which, in the case of the corneal collagen fibers, would cause an opaque cornea. It has been previously demonstrated that the tight collagen packing within the normal, clear cornea, confirms that the fibers do not independently scatter light. If each collagen fiber is perfectly arranged, then the relative phases and intensity of each scattered wave fields can be calculated and if the distance between collagen fibers is less than the light wavelength, then the light scattered intensity is essentially zero.

It has been previously demonstrated that perfect arrangement is unnecessary. Only a limited amount of correlation is necessary to produce transparency. The uniform density of scatterers is necessary for transparency. Like the cornea, the lens of the eye consists of densely packed and uniform lens proteins and is transparent. Unlike the cornea, the lens index of refraction changes according to the anatomical location within the lens. The refraction results from scattering caused by the constructive interference of the scattered light.

Light scattering results from changes in density. The random fluctuation in density is the sum of many sinusoidal waves, also called Fourier components. When a density fluctuation causes light scattering only Fourier components with wavelengths greater than one half the wavelength of light cause the scattering. The collagen fibers are much larger in the sclera than the cornea. The collagen diameters and fiber spacing are comparable to the wavelength of light resulting in extensive light scattering, turbidity, and an opaque sclera.

The retina exhibits a semi-regular cell arrangement packed together within small distances as compared to the light wavelength resulting in retinal transparency.

Light Scattering in the Eye

Cornea—The normal cornea accounts for 10% light scattering which is why it can be studied with a slit lamp biomicroscope. The corneal epithelium where the cells are held tightly together with minimal intercellular spacing cannot be visualized. The refractive index is essentially stable so the cells appear transparent.

Lens—The normal lens absorbs visible blue light and has a slight yellow color which deepens with age. 3 percent of the incident light is back scattered.

Vitreous—The vitreous body consists of hyaluronic acid molecules and collagen fibrils which are approximately 100 Å in diameter, much smaller than the normal corneal collagen fibers. Only approximately 0.1% of incident light is scattered.

Retina—The slight changes in refractive indices are small in comparison to the wavelength of light which is why the retina is transparent. The fundus is visible due to the reflection from the retinal pigment epithelium and choroid. In order to quantify the retina light scattering, a light scattering goniometer has been previously constructed using a tunable supercontinuum laser which illuminated a 50μ spot on an in vitro squirrel retina. The findings from use of this device confirmed that the scattering coefficient was much greater in the choroid and sclera than the retina. As expected, scattering decreased with wavelength. Only the retinal pigment epithelium and choroid display absorption. Anisotropy is higher in the retina than the other structures.

2. Dynamic Light Scattering Spectroscopy

Dynamic Light Scattering (DLS) Spectroscopy, also known as Photon Correlation Spectroscopy (PCS), Quasielastic Light Scattering Spectroscopy (QLS), or Laser Light Scattering (LLS) Spectroscopy measures the thermal random movement (Brownian Motion) of particles by analyzing the temporal fluctuations of in scattered light intensity. The random motion of proteins causes local concentration changes which affects the intensity of scattered light. The scattered light intensity I(t) is compared to the scattered light intensity at a later time, τ, measured as a time correlation I(t+τ):<I(t)I(t+τ)> where < > is averaging over beginning time t. Scattered waves interference in the far field region generates a net scattered light intensity I(t), which displays stochastic fluctuations depending on whether the interference is constructive or destructive due to the random motion undergone by suspended particles. DLS assumes that each detected photon has been scattered once.

There is a high correlation with short time delays; the signals are unchanged because the particles do not have a chance to move. With a longer time delay, the correlation will decay exponentially. A monodisperse sample will exhibit a single exponential decay.

$$g(q; \tau) = \exp(-\Gamma\tau)$$

where Γ=the decay rate. The translational diffusion coefficient $D_t$ may be derived at a single angle or at a range of angles depending on the wave vector q.

$$\Gamma = q^2 D_t$$

with $$q = \frac{4\pi n_0}{\lambda}\sin\left(\frac{\theta}{2}\right)$$

Where:

λ is the incident laser wavelength $n_0$ is the sample's refractive index

θ is angle at which the detector is located with respect to the sample

Small spherical particles do not demonstrate angular dependence or anisotropy. Non spherical particles demonstrate angular dependence and anisotropy. An optimum angle of detection θ exists for each particle size. This is important in a polydisperse sample with an unknown particle size distribution. The autocorrelation function is a sum of the exponential decays corresponding to each of the species in the population.

Cumulant method—The cumulant method calculates the exponentials and system variance.

$$g(q; \tau) = \exp\left(-\Gamma\left(\tau - \frac{\mu_2}{2!}\tau^2 + \frac{\mu_3}{3!}\tau^3 + \dots\right)\right)$$

where:

Γ is the average decay rate $\mu_2/\Gamma^2$ is the second order polydispersity index (variance)

The cumulant method is less affected by experimental noise. Simply explained, a least-squares fit is made of a polynomial in t to the logarithm of C(t), after the baseline is subtracted. D is the coefficient of the linear term which approximates the average particle diffusivity. An approximate particle diameter may be obtained by utilizing the Stokes-Einstein equation. A digital autocorrelator obtains C(t) simultaneously resulting in a smooth function. With uniform particles and baseline subtraction, there is a single decaying exponential.

$$C(t) = A \cdot e^{-2DK^2 t}$$

$$K = \left(\frac{4\pi\eta}{\lambda}\right)\sin\left(\frac{\theta}{2}\right)$$

Where:

n=index of refraction of solvent

One obtains D from the decay constant. Rh, the hydrodynamic radius of the particles, is obtained by the Stokes-Einstein equation.

$$R_h = \frac{kT}{6\pi\eta D}$$

Where:

k=Boltzmann's constant

T=absolute temperature

η=shear viscosity of the solvent

The cumulant analysis method can be simple to use. The most accurate results are achieved when applied to unimodal scattering particles with a relatively narrow size distribution. It can also provide information regarding the polydispersity of the macromolecular distribution. The problems with this method are that it is unable to distinguish between a bimodal and a broad continuous distribution using a single sample time. Also, if there is a significant percentage of larger or aggregated particles, they will act as strong scatters and may disproportionately weight the correlation function. In this case the diffusion coefficient will reflect the motion of the larger scatters without reflecting concentrations relative to the smaller scatterers.

CONTIN algorithm—CONTIN uses an inverse Laplace transform to analyze the autocorrelation. It is best utilized for multimodal, heterodisperse and polydisperse systems. The resolution for separating two different particle populations is approximately a factor of five or greater. The difference in relative intensities between two different populations should be less than $1:10^{-5}$.

3. Animal Experiments

The first in vivo study utilizing DLS was performed by Nishio, Weiss, Tanaka, et al. at M.I.T. in 1984. In this experiment, 8 New Zealand White rabbits received 2000 rads of X-irradiation (85 kVp, 5 mA) to one eye at 5 weeks of age. Matsuda, Giblin and Reddy, in 1981, previously demonstrated that the X-irradiated lens develops posterior subcapsular opacification 3 weeks after irradiation and a mature cataract 5-6 weeks later.

A DLS system was used to perform measurements from 8 irradiated and 4 non-irradiated control rabbits. Two irradiated rabbits were subsequently euthanized and in vitro measurements were performed. Only one eye of the rabbit was irradiated, the other eye was used as a control.

At each age, the correlation function of the lens nucleus decayed more slowly than the cortex in the normal, non-radiated rabbit with clear lenses. Older rabbits demonstrated a much slower correlation time than the younger rabbits. There was a significant decrease in correlation time as the rabbit aged from 6 to 12 weeks.

A dramatic change was observed in the correlation function of the nuclear region even 2.5 weeks after irradiation with a clear lens. The change was confirmed by both non-radiated rabbit and the opposite non-irradiated eye of the irradiated rabbit.

There was a change in the average correlation times as a function of position with the proteins at the posterior pole of the lens demonstrating a marked change in diffusivity consistent with the appearance of a posterior subcapsular cataract. The correlation time at the normal lens nucleus was larger than that found in the X-irradiated lens.

The paper from the study showed that the in vivo measurement of lens proteins can detect cataractous changes prior to visible changes in lens turbidity.

4. Ocular Anatomy

Simplistically, the eye has been compared to a camera. The cornea and lens of the eye focus light onto the retina, or the "film in the camera." The optic nerve carries the image to the brain, like a cable to a computer monitor, for interpretation. A physician looking into the left eye of a patient with an ophthalmoscope will see the optic disc appearing as a circular object and the macula as a reddish structure. The fovea appears as a slightly clearer object in the center of the macula. The retinal veins are seen slightly wider and deeper in color than the arteries. In the right eye, the location of the optic disc and the macula appear reversed.

The human retina consists of 10 layers. Starting inside the eye, moving backwards or posteriorly the layers are:

1. Inner limiting membrane—basement membrane consisting of Muller cells.
2. Nerve fiber layer—this layer represents the axons, similar to "wires" coming from the ganglion layer below, that enter the optic nerve and transmit their messages to the brain.
3. Ganglion cell layer—this layer contains the nuclei of the ganglion cells and some amacrine cells.
4. Inner plexiform layer—contains the connection, or synapse between the bipolar cell axons and the connection structures, or dendrites of the ganglion and amacrine cells.
5. Inner nuclear layer—contains the nuclei and the cell bodies of the bipolar cells.
6. Outer plexiform layer—the ends of the rods and cones (the photoreceptors) make synapses, or connections with the dendrites of the bipolar cells.
7. Outer nuclear layer—contains the cell bodies of the rods and cones.
8. External limiting membrane—separates the inner segment of the photoreceptors from their cell nucleus.
9. Photoreceptor layer—contains the rods and cones.
10. Retinal pigment epithelium—a layer of cells.

The retina and optic nerve are part of the central nervous system (CNS) and are the only parts of the CNS that can be directly visualized. The image one sees is not just displayed on the retina, it is processed in the retina. In this respect the retina is more like a computer than a simple film in a camera.

Light passes from the left (the front of the retina) through the nerve layers to reach the rods and the cones on the far right. A chemical change occurs in the rods and cones which sends a signal to the nerves. The signal is processed by the bipolar and horizontal cells, to the amacrine cells and ganglion cells, and then to the optic nerve fibers which go to the brain. The retina contains approximately 7 million cones, and 75-150 million rods. The cones are utilized in daylight, and for color vision, the rods in dim light and black and white vision. The human eye contains one fovea, the depression in the retina in charge of sharp central vision. The fovea is dominated by cones, the peripheral retina by rods. When one is reading, they are using their central vision and if someone walks into the room, they will be aware of this by the stimulation of their peripheral vision. The most accurate information is provided by the fovea, which although it represents less than 2 degrees of visual angle, is connected to 10% of the axons of the optic nerve.

Since there are 100 times the number of retinal receptors as there are nerve fibers in the optic nerve, a large amount of signal processing must be performed in the retina. Images are compressed to fit the optic nerve capacity. The bipolar and ganglion cells perform "center surround processing" which are "on" and "off" centers. "On" centers are positively weighted in the center and negatively weighted around the center. "Off" centers are the opposite. They function similar to a mathematical algorithm in enhancing the edges of an image.

5. Human Studies

The first DLS trial was reported by Weiss and Rand, et al. in 1983. A significant correlation was found between the diffusion coefficient and patient age (p<0.05). The age adjusted mean diffusion coefficient for nondiabetics (4.60+/−0.29; mean+/−SEM) was significantly higher compared to diabetics without retinopathy (3.59+/−0.41; P=0.0473), diabetics with background or pre-proliferative retinopathy (2.73+/−0.27; P=0.0001), or to diabetics with pre-proliferative or proliferative retinopathy receiving laser photocoagulation within 1 year of measurement (3.02+/−0.37; P=0.0012). Diabetics with laser treatment more than 1 year prior to measurement (3.96+/−0.51) did not differ significantly from nondiabetics. In summary, DLS measures the Brownian movement of protein within the retina. The movement slows down as the person ages and slows down even further, similar to an older nondiabetic person, in a patient with diabetes.

Bursell, Baker, Weiss, et al. performed DLS measurements on 393 diabetic patients and 38 non-diabetic patients attending the Joslin Diabetes Center Eye Unit. In order to evaluate the contributions of different protein size distributions measurements were made at 1.5 μs and 150 μs sample times. The previously discovered decrease in lens protein diffusion coefficient with age was confirmed. Age-adjusted analysis of covariance demonstrated that clinically observable nuclear sclerosis was significantly associated with a decreased diffusion coefficient. The presence of diabetes, degree of diabetic control, duration and age of onset of diabetes, and type of diabetic therapy were all significantly related to changes in the measurements of lens proteins. The lens proteins are a polydisperse collection of scatterers with correlations from $1\mu$ to 1 ms sample times.

Four, 5 second measurements from the lens nucleus were taken at 1.5μ and 150 μs sample times. At the 1.5 us sample time in a young group the diffusion coefficient ranged between $1.6 \times 10^{-7}$ cm$^2$/s and $6.4 \times 10^{-8}$ cm$^2$/s. The calculated hydrodynamic radii for these proteins is from 135-300 Å, which is comparable to the size of alpha-crystallin. In older subjects the calculated hydrodynamic radii was between 300 and 7000 Å, consistent with the conversion of smaller alpha-crystallin into greater molecular weight aggregates. The finding is consistent with biochemical studies demonstrating a decrease in alpha-crystallin monomers in the aging lens nucleus. The study confirmed prior epidemiological studies demonstrating the earlier onset of cataracts in diabetic patients as compared to non-diabetic patients, and a diminishing risk with progressive age.

Bursell, Weiss, et al. also performed DLS measurements to monitor the effect of transient blood glucose changes on diabetic patients undergoing glucose clamping protocols and nondiabetic patients undergoing glucose tolerance testing. The diabetic patients did not exhibit an acute change in diffusion coefficient in response to acute blood glucose changes presumably the result of osmotic buffering which ameliorated the change in aqueous glucose levels. The nondiabetic patients demonstrated a biphasic change in lens diffusion coefficient secondary to glucose loading. Initially, there was a decrease in diffusion coefficient followed by an increase to a maximum approximately 30 minutes after peak blood glucose. 60 minutes later, the diffusion coefficient returned to the baseline level. The noted changes are presumably the result of changes in lens hydration in response to glucose loading.

In the prior studies, DLS measurements were made from the lens of the eye. Weiss, Bursell, et al. performed measurements from the corneal stroma of diabetic and nondiabetic patients. Changes in measurements were noted as a result of aging, and in diabetic patients with proliferative diabetic retinopathy. Diabetic patients with proliferative diabetic retinopathy, who had undergone successful panretinal laser photocoagulation with resolution of the proliferative diabetic retinopathy had measurements similar to nondiabetics or to diabetic patients without retinopathy, or with minimal background diabetic retinopathy.

SUMMARY OF THE INVENTION

The present invention attaches a Dynamic Light Scattering (DLS) device to one, as an example, of many ophthalmologic instruments, as well as to goggles, to enable the DLS measurements to be performed. Thus, in one non-limiting embodiment a novel DLS machine is provided that permits for the making of retinal measurements.

Using the novel DLS machine, the inventor conducted the first study utilizing retinal DLS measurements in patients receiving intravitreal injections of either Avastin, Lucentis, or Eylea for wet age-related macular degeneration. Patients receiving these injections underwent DLS measurements over the course of 6 months to determine whether the measurement could predict the redevelopment of subretinal fluid in patients receiving these medications.

The study results may be summarized as follows:

1. Each patient is their own control
2. If the right eye (OD) or left eye (OS) fundus is normal, then the measurements between the two eyes are within a few percent of each other.
3. DLS measurements are reproducible over time.
4. DLS measurements decrease in eyes requiring the anti-VEGF medication and anticipates or predicts the development of subretinal fluid.
5. The DLS measurement increases in those patients with successful response to injections with a decrease in subretinal fluid and decreases in those patients requiring additional injections.
6. DLS measurements anticipate OCT results.
7. DLS measurements more accurately mirror visual acuity than does OCT.
8. Increased DLS measurements and increased visual acuity is observed, even if the OCT measurement is unchanged.
9. Eyes that have received Avastin or Lucentis, even if stable, have a lower DLS measurement than the fellow, untreated eye. The observed lower DLS measurement is similar to that obtained in patients diagnosed with geographic atrophy.
10. Eyes that received Eylea, did not exhibit the significant decrease in DLS measurements seen in patients receiving either Avastin or Lucentis.

The novel DLS machine is also being used by the inventor in a study for detecting dementia.

Alzheimer's, researchers are studying the effect of genetic, environmental, dietary, infectious agents and metabolic abnormalities that may lead to the diseases' development. Unfortunately, there is no clinical test to diagnose this condition. Posthumously, neuritic plaques composed of amyloid protein and/or neurofibrillary tangles of tau protein are found. The average life expectancy following diagnosis is five to ten years. There is no successful treatment, drugs may improve symptoms in some cases. In the last decade, more than 500 drug studies have failed to find a treatment for this condition. In the absence of a definitive quantitative endpoint, most studies have been terminated after 2 years, yet it would take more than 5 years to determine a meaningful effect.

Parkinson's disease is a degenerative disorder of the central nervous system. Early symptoms are tremor, rigidity and difficulty walking. Cognitive and behavioral problems occur and dementia is common in the advanced stages. Parkinson's disease typically occurs in people over the age of 60. Males are more often affected than females. The average life expect following diagnosis is between 7 and 15 years. No cure for PD is known; early treatment aims to reduce the effects of the symptoms.

The eye is the only place in the body where an artery, vein, and nerve can be directly visualized. The nerve fiber layer of the retina is an outgrowth of the brain. Recent research has determined that the retina is affected by Alzheimer's disease. Specifically, retinal thinning is noted by noninvasive Ocular Coherence Tomography testing. A much earlier molecular effect must lead to an imaging change. Retinal thinning will lead to a slowing of the Brownian movement of the retinal proteins. This finding has been confirmed by DLS testing and in addition, a slowing of the Brownian movement of the retinal proteins has been seen in recently diagnosed dementia patients in the absence of retinal thinning by OCT testing.

1. Reproducibility—In a recent study 17 patients were tested. There was no significant difference between measuring from the macular area from either the left or the right eye. No differences in measurements were seen between men and women. 8 patients were tested 3 and 6 months later—there was no significant difference between the 1, 3, and 6 month measurements.
2. Sample times—Measurements were made at 12.5, 200, 400, 800, 1600, and 3,200 nanoseconds. The best fit measurements were seen at the 12.5 and 200 nanosecond sample times. This finding is consistent with the most accuracy. This finding was confirmed in all cohorts tested.
3. Measurement duration-Successful measurements may be made at 2 second durations in cooperative patients. However, the consistently best measurements were made with a 5 second duration.
4. Dementia 15 patients/25 controls (age-matching)

Retinal measurements—Measurements were made from the macular area. In order to remove the effect of any local retinal pathology on the DLS measurements, such as diabetic macular edema, or age-related macular degeneration, measurements were also made from 5 patients at the optic nerve. This "proof of concept" demonstrated measurements that were similar to those taken from the normal retina. An advantage of optic nerve versus retinal measurements would be that a retinal examination is no longer required. Also, the measurement may be automated such that no operator is required.

Accordingly, it is one non-limiting feature of the invention in at least certain embodiments to attach an incident laser light or other coherent light source, a fiber optic and a detection fiber optic of the disclosed DLS device to the front end of an ophthalmologic instrument, including, without limitation, a fundus camera, ocular coherence tomography (OCT), therapeutic laser device, other ophthalmic diagnostic or treatment machine, or to goggles, or eyeglasses, so that the DLS laser beam may be visualized within the ocular of the ophthalmic diagnostic or treatment machine, and/or the beam is parfocal or in focus with the light of the diagnostic or treatment ophthalmic device, and/or is visualized by the patient. A nonmydriatic optical system may be utilized. Self-focusing and image stabilization may also be utilized. The measurement may be automated such that no operator is required.

Accordingly, it is one non-limiting feature of the invention in at least certain embodiments to detect the onset of neurologic disease before the onset of clinical symptoms.

It is another non-limiting feature of the invention in at least certain embodiments to study the effectiveness of various medications on the neurologic disease.

It is a further non-limiting feature of the invention in at least certain embodiments to provide a method where the appropriate threshold or time for the delivery of the therapeutic intervention to be the most efficacious may be discovered.

Another non-limiting feature of the invention in at least certain embodiments is to monitor the effectiveness of therapeutic interventions to treat ophthalmic conditions and diseases.

The foregoing non-limiting features can be achieved from the calculation of the diffusion coefficient from the retina of a patient's in vivo eye by directing a beam of light from a low-power laser or other coherent light source at a spot in the retina or choroid of the patient's eye and measuring the fluctuations in the intensity of the back-scattered light. A number of measurements are taken from the retina or choroid of normal or disease-free patients of similar ages to establish a database, such as but not limited to, an electronic database, for comparison with the abnormal results. In addition, or alternatively, the subject may be analyzed over time to determine changes in the measurement from an initial or baseline measurement or taken before and after a therapeutic intervention. The diffusion coefficient or another calculated term may be used to diagnose, measure the severity of the disease, monitor the progress and treatment of the condition, or assess the efficacy of therapeutic interventions. The measurement may be utilized with or compared with an Ocular Coherence Tomography (OCT) image and measurement also made from the same or nearby area of the retina.

The apparatus used to perform this method may include a low-power laser or other coherent light source and associated optics attached to a commercially available fundus camera. Utilizing the optical pathway of the fundus camera precludes the necessity of using a contact lens to focus light on the retina. A flat contact lens may be used to stabilize the eye and prevent eye movement during the measurement, but is not considered necessary.

An infrared viewing light may be used to aid in the maintenance of the measuring spot on a specific area of the retina or choroid when the visible light of the fundus camera is deactivated during the performance of the measurement. An automatic focusing and alignment system may be utilized. The location chosen for measurement may also be made on the basis of fundus autofluorescence, fundus fluorescein angiography, OCT or another imaging technology.

The device may be incorporated with or within an OCT device so at one sitting, both measurements/tests may be made from the patient. A digital photon counter is used to detect fluctuations in the intensities of the back-scattered light and a digital correlator is used to process the output of the photon counter to provide a set of numbers that can be used to calculate the diffusion coefficient or another mathematical term.

As part of the diagnostic process, patients may undergo an ophthalmic examination to exclude confounding eye diseases. An OCT image and measurement may be taken to aid in the determination and location of retinal thickness and to exclude pathology that would affect the DLS measurement. A cognition test, such as a Mini-Mental State Exam may also be performed.

BRIEF DESCRIPTION OF THE DRAWINGS

FIG. 4 illustrates a non-limiting listing of the attachment parts;

FIG. 7 illustrates a headset which can be modified with attachments for the incident fiber optic that provides the light, and the detection fiber optic that measures the back-scattered light, arranged vertically in front of the left eye in accordance with the present disclosure;

FIG. 8 illustrates that when the face plate can be rotated 180 degrees, the fiber connectors can be rotated from the patient's left eye to the right eye in accordance with the present disclosure;

FIG. 9 illustrates rotating the two connectors in a horizontal fashion;

DETAILED DESCRIPTION

Figure 1:
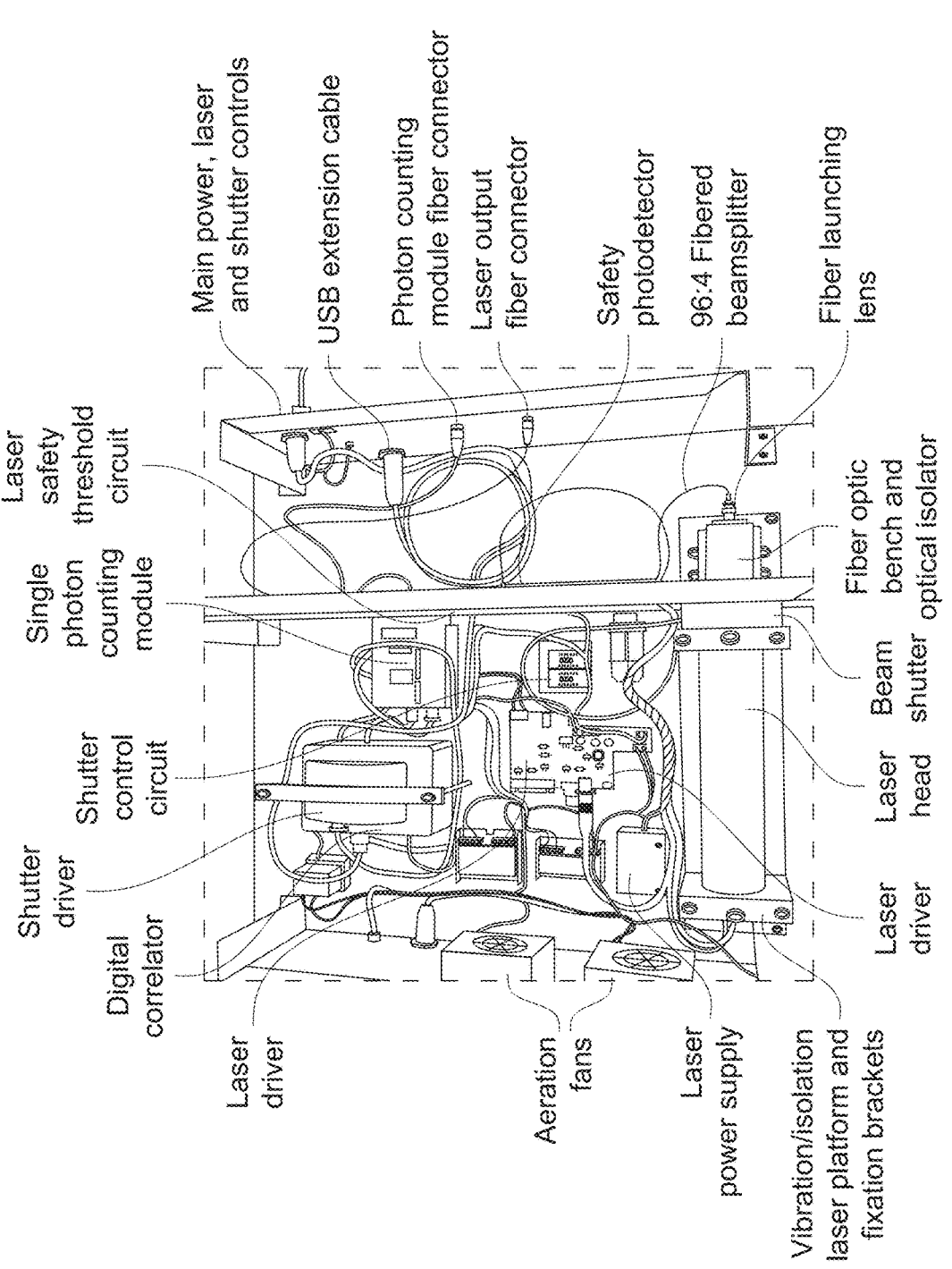
FIG. 1 shows a non-limiting embodiment of the electronic components in accordance with the present disclosure.

In FIG. 1, the light source part of the apparatus can consist of laser 200, laser safety threshold circuit 205, and shutter assemblies 210 and 215. Laser 200 can be an approximately 1.5 milliwatt helium-neon laser of conventional design that is commercially available from several companies. The laser output provides an optical power to the patient below the maximal permissible exposure recommended by the American National Standards Institute, ANSI Z136.1 (2014) standard. The minimal amount of light necessary to make a successful measurement is used and may be determined by experimentation.

Figure 2:
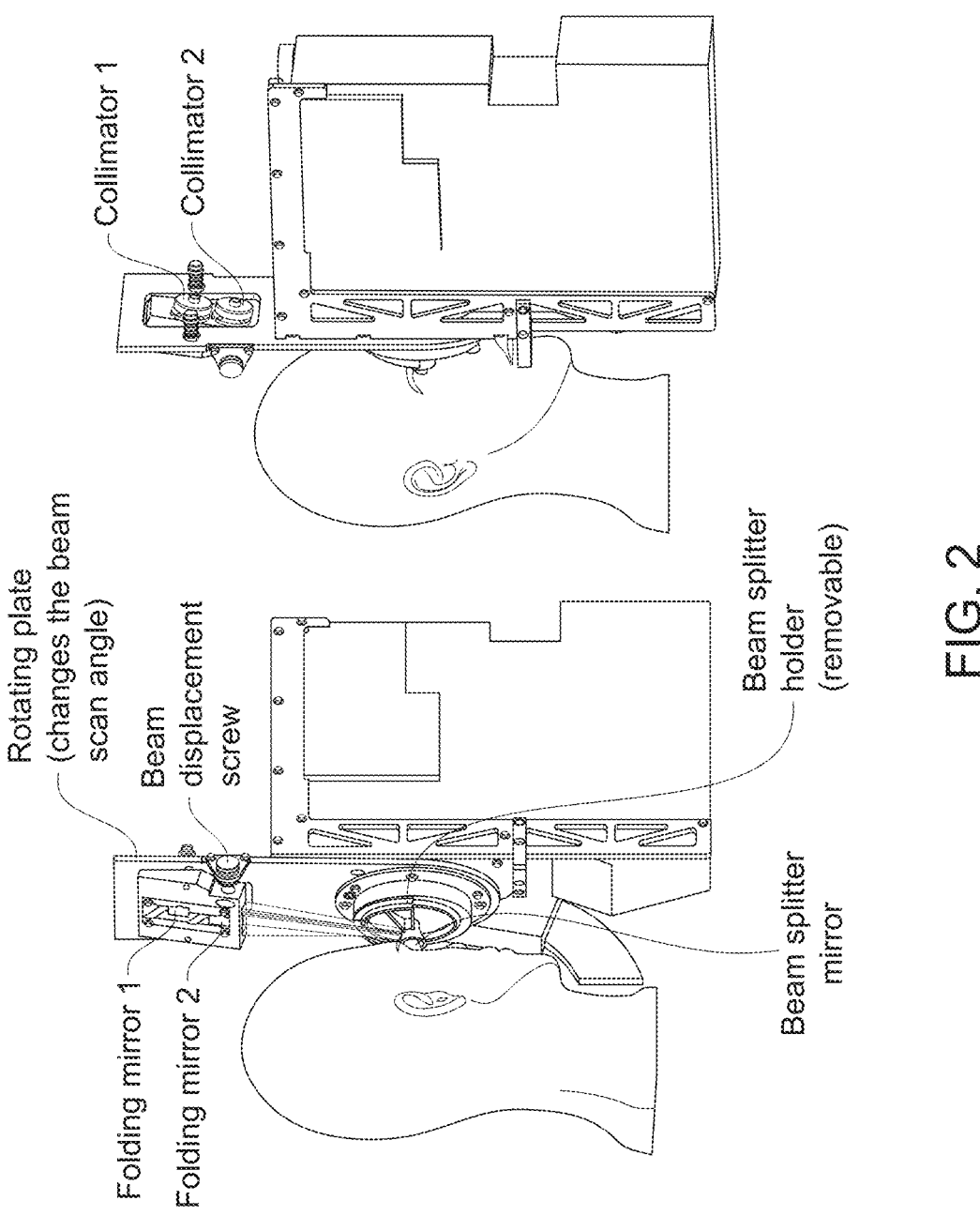
FIG. 2 illustrates a non-limiting attachment of the attachment components in accordance with the present disclosure.

In FIG. 2, light passing through optical fiber 220 is mounted in termination 225 that is attached to a linear positioner 230 on the fundus camera attachment 235. The positioner is available to vary the measurement spot on the retina. Mirrors 240, 245 and a beam splitter 250 are provided to place the incident beam into the frame of the fundus camera (as a non-limiting example) image of the retina.

The detection optical fiber 255 attached to the linear positioner 230 on the non-limiting example fundus camera so both the incident light and detection light is simultaneously varied by the same amount. The light output of detection fiber 255 is detected by single photon counting module 260 and processed by the correlator software on a personal computer. The laser preferably goes through the incident fiber and the backscattered light from the retina and/or optic nerve is detected by the detection fiber.

Optics may be incorporated to vary the diameter of the beam on the retina or choroid thus allowing a greater or smaller area to be sampled or measured. Modifications may also be made to the detection fiberoptic such that a smaller or larger measurement area may be made.

The optical arrangement is attached to a frame that is easily connected to a commercially available instruments, such as an OCT, fundus camera, laser treatment device, or other devices. These devices are typically used in ophthalmological studies and treatments of the eye. Ophthalmologic devices suitable for modification are manufactured by multiple companies and the conventional operation and use of those devices is performed by ophthalmologists and others engaged in the examination of human eyes. The attachment of the disclosed device can be sized to fit the chosen ophthalmic device. Alternatively, the incident and detection fiber optic may be directly attached to the front surface of a Virtual Reality headset, Augmented Reality headset, a headset, goggles, or eyeglasses, so that the patient may visualize the incident light and the detection fiber may detect the backscattered light from the retina and/or optic nerve Also, the laser diodes utilized within the OCT device may also be used to perform the DLS measurement. If infrared diodes are utilized, then pharmacologic dilation of the pupil may not be necessary to perform the DLS measurement. A device to maintain fixation and/or focusing of the incident light in the presence of eye movements may be utilized.

A fundus camera consists of a light source, a viewing microscope and a mechanical supporting arrangement that allows precise positioning of the light source and microscope relative to the patient to enable focusing and visualization of the light on selected portions of the patient's eye in order to perform photography. One non-limiting fundus camera that can be used with the present invention is manufactured by Topcon Inc. of Japan.

Figure 3:
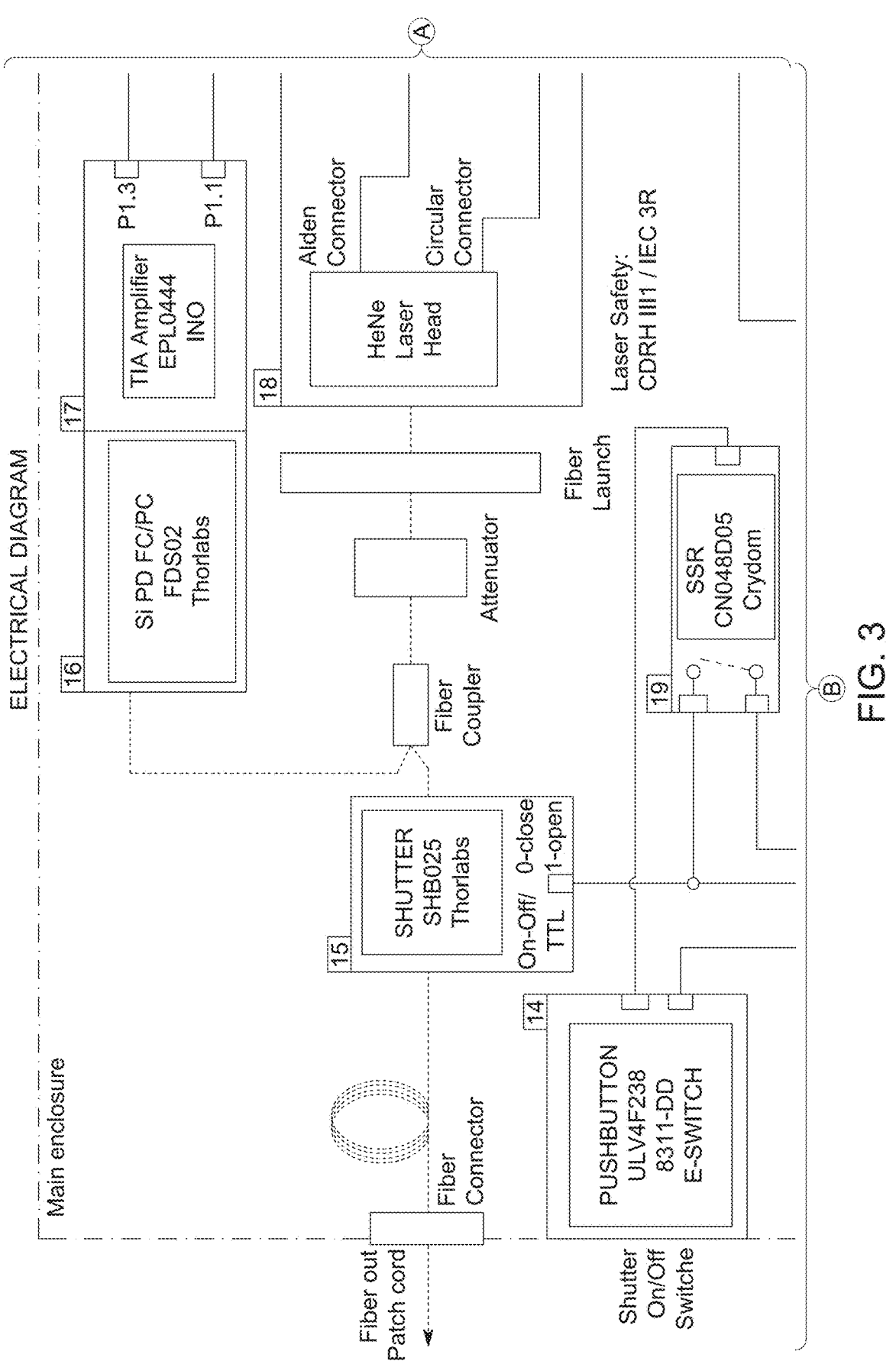
FIG. 3 details a non-limiting embodiment of the electrical components in accordance with the present disclosure.
Figure 3:
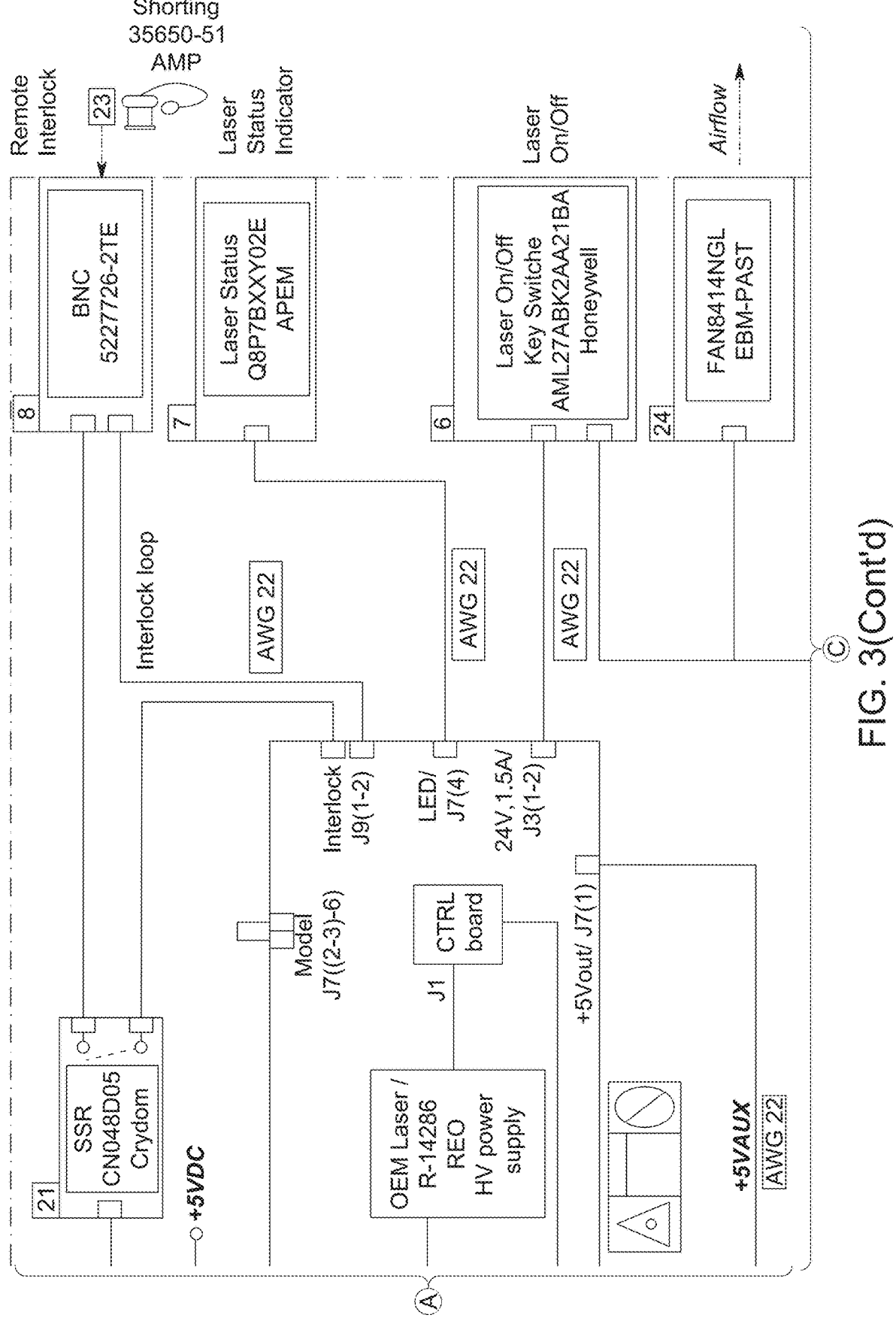
Figure 3:
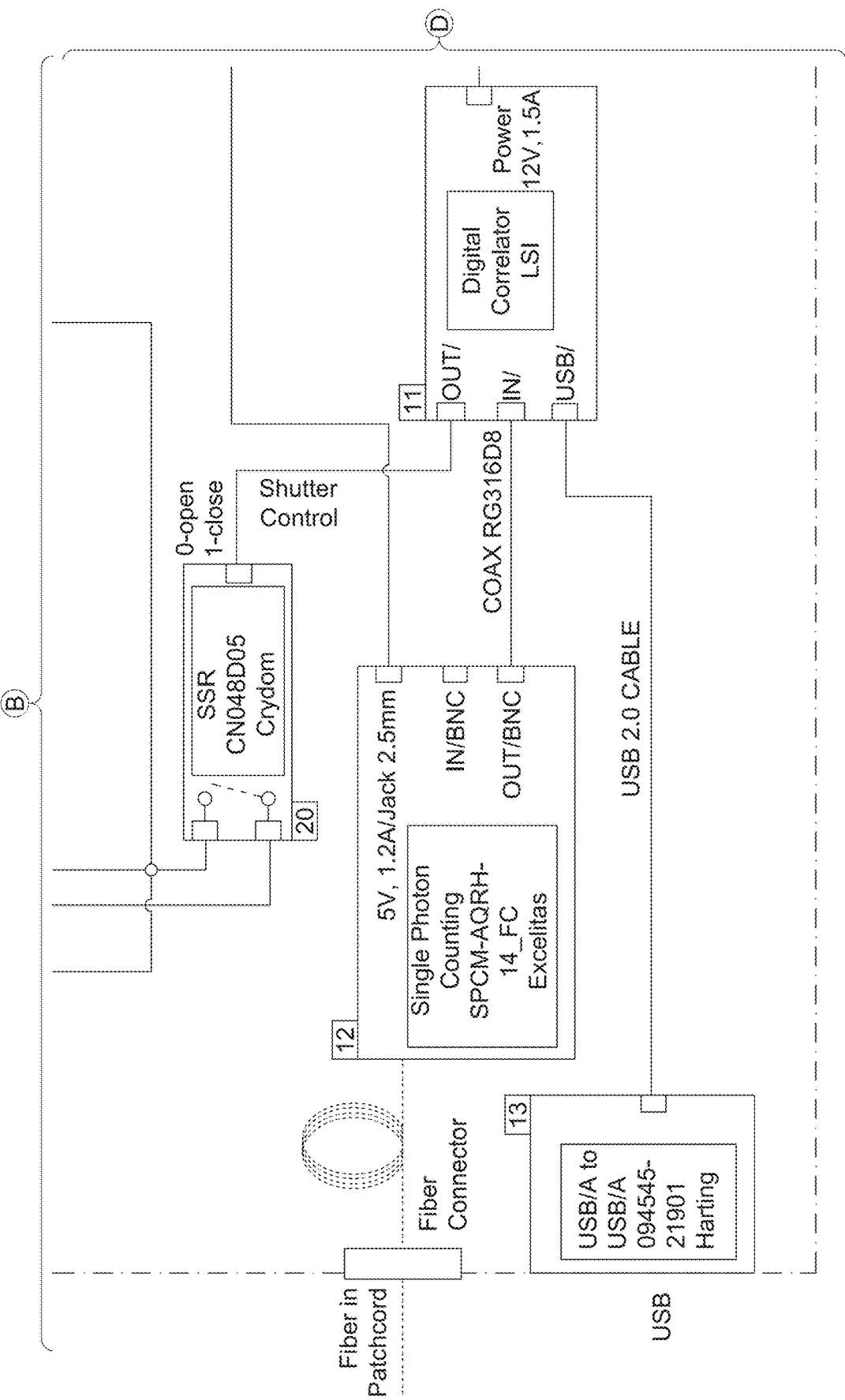
Figure 3:
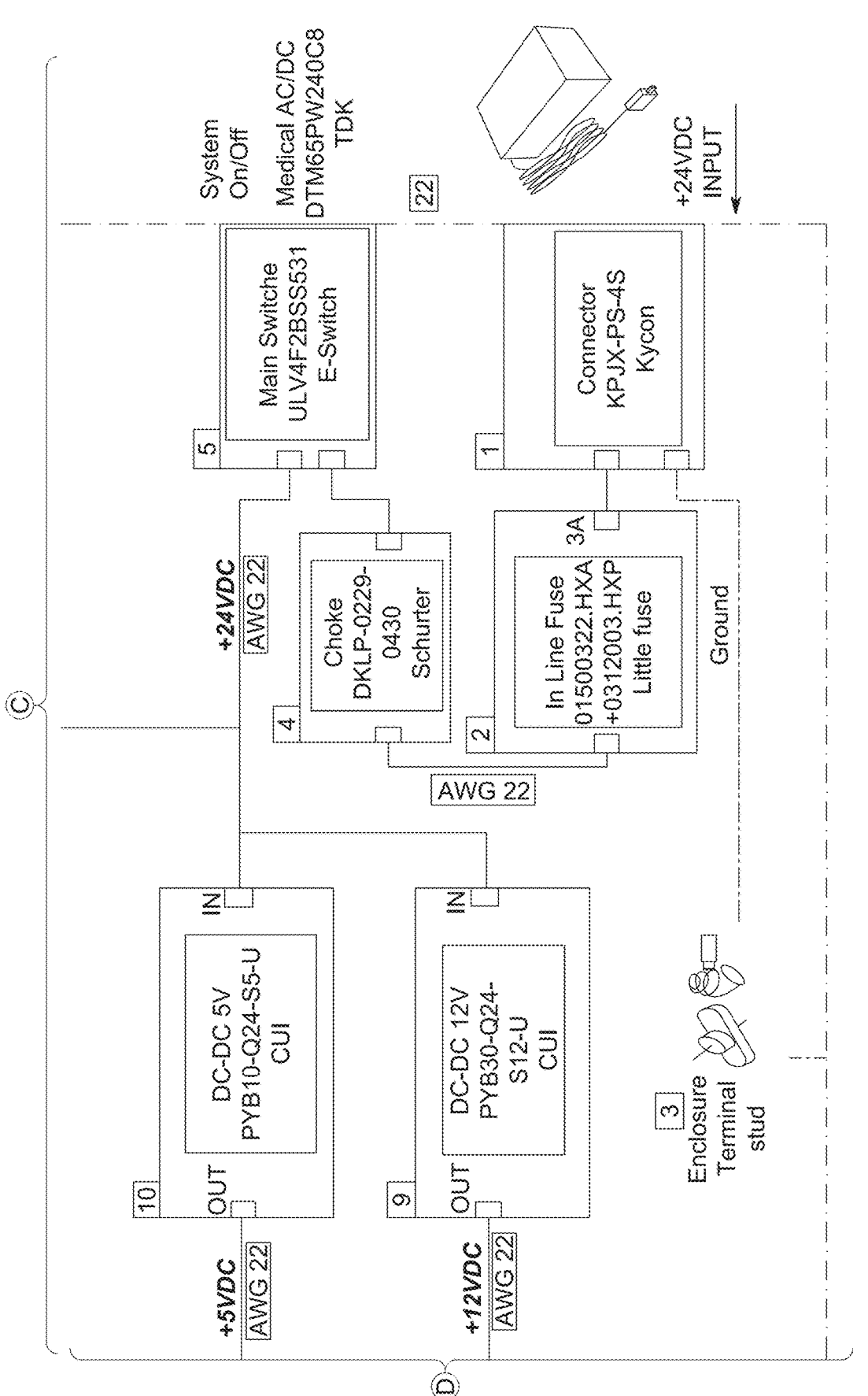
Figure 5:
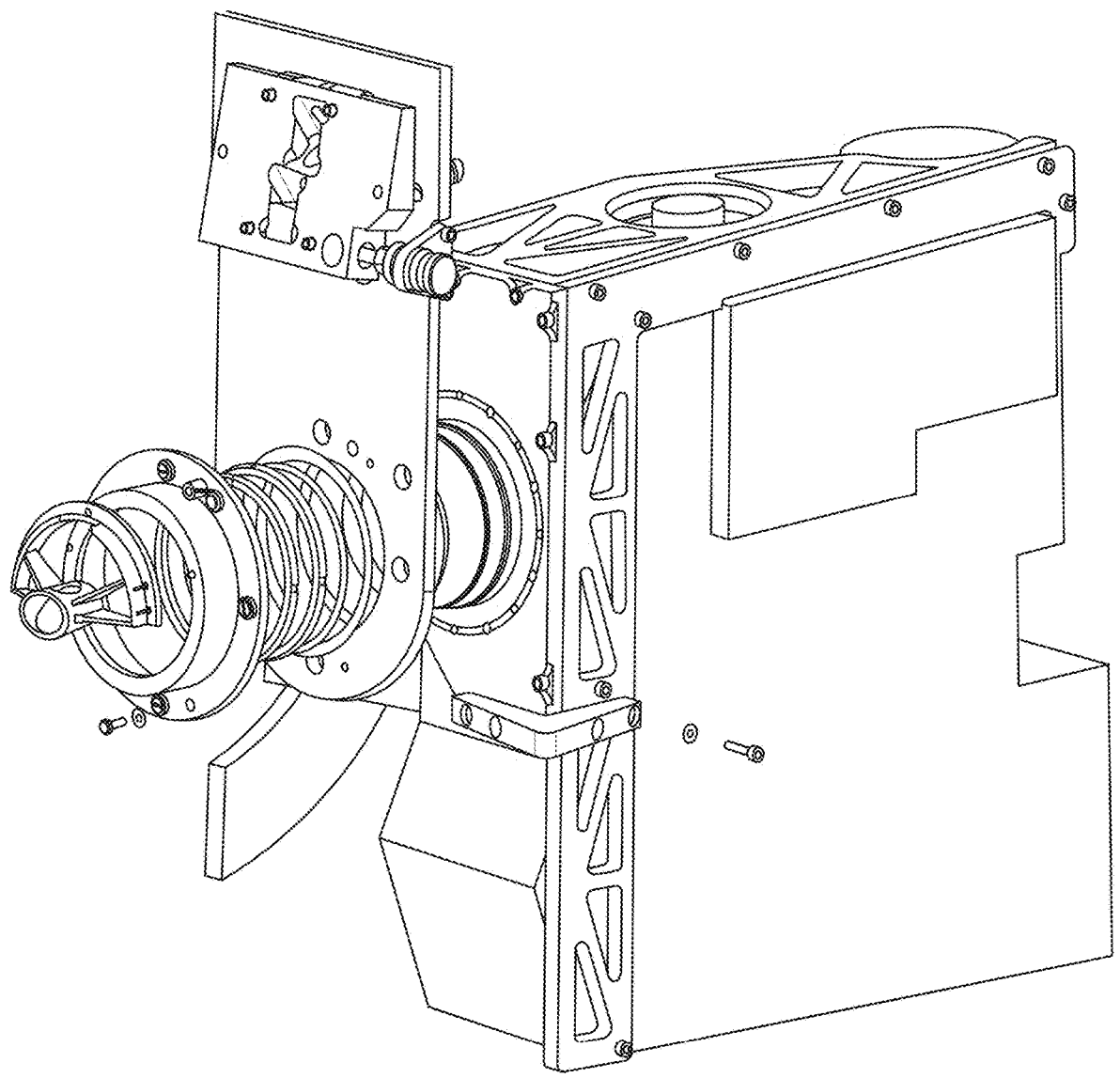
FIG. 5 shows a break-down diagram of the anterior attachment parts.
Figure 6B:
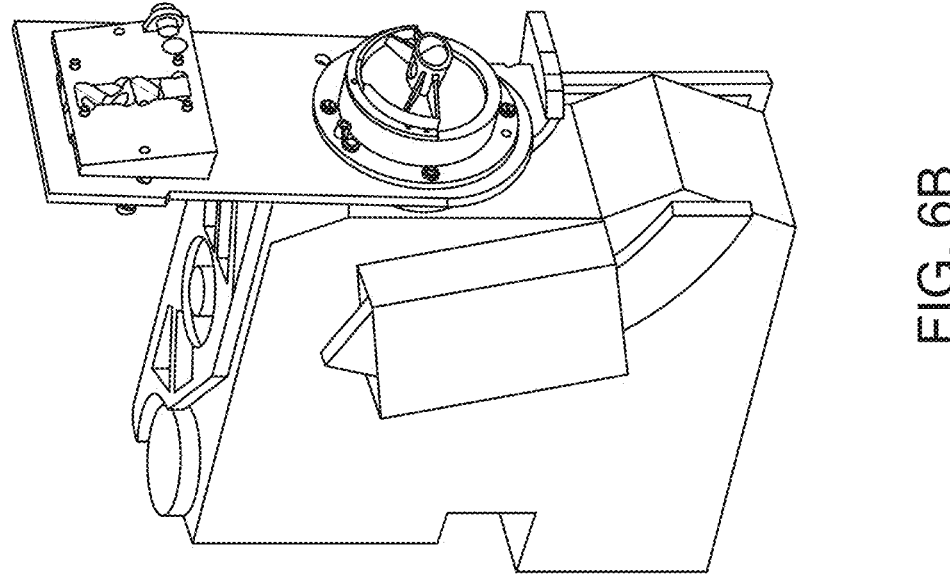
FIG. 6B illustrates a left side perspective of the non-limiting camera that can be used in accordance with the present disclosure.
Figure 6A:
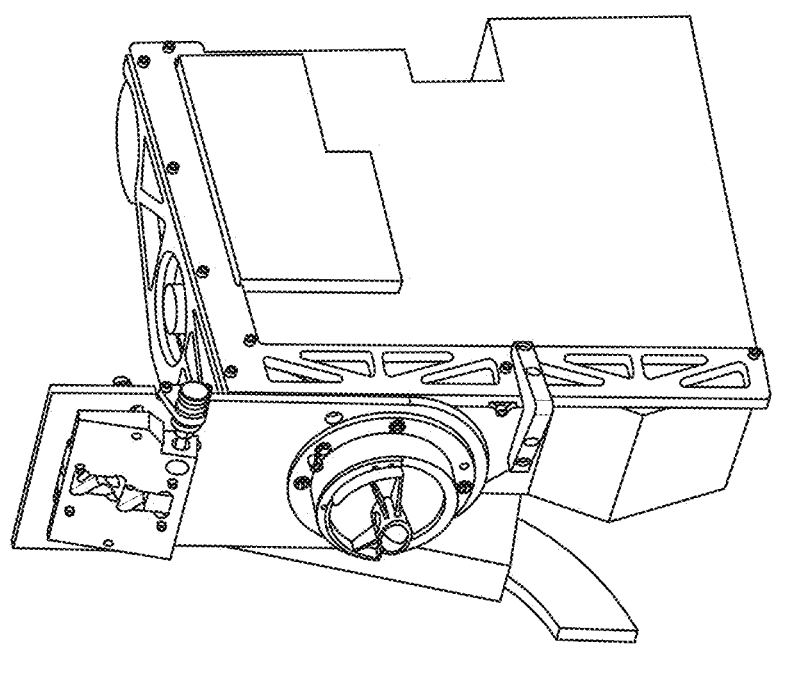
FIG. 6A illustrates a right side perspective of a non-limiting camera that can be used in accordance with the present disclosure.

In FIG. 3, non-limiting details of one embodiment for the electrical components used in this device are seen.

In still another embodiment, the described device may be incorporated with another device used in ophthalmology, such as, but not limited to, an Ocular Coherence Tomography (OCT) machine, that can provide the incident light and focusing on the eye necessary to the performance of the method.

In another embodiment the operation of the device or devices may be automated, such that an operator is not required to make the measurements.

Correlator 265 counts for a predetermined time interval and performs a well-known mathematical operation to obtain the correlation function. A suitable time interval can be approximately five seconds, though another measurement duration may be selected by experimentation. The sample time may be chosen to further characterize the population of light scatters. Measurements taken at shorter sample times, i.e., at 1.5 microseconds, appear to be more characteristic of smaller and/or faster scattering elements whereas measurements made at longer sample times, i.e., 200 microseconds, appear more characteristic of larger and/or slower scattering elements. Multiple measurements may be taken and the results averaged to minimize artifacts. The correlator utilizes the received counts to solve the following equation for the autocorrelation function Cm(t):

$$C_m(t) = \sum_{i=1}^{i=n} P_i P_i + m$$

where:

t=the length of the predetermined time interval i=an index number whose range is one to the total number of intervals $p_i$=the number of pulses occurring during the ith time interval n=the total number of intervals m=an integer whose range is the number of correlator channels In accordance with the above equation correlator 265 produces solutions or points (one for each value of m) in a time sequence, each measurement separated by the value of t. These measurements may be plotted against time to produce a curve that may then be displayed for examination on a personal computer monitor.

More specifically, the program calculates the first and second cumulants (and their respective statistical uncertainties) of the decay rate distribution from a weighted least squares fit of the measured autocorrelation function. Calculations are performed using the results of the cumulants analysis to yield the average translational diffusion coefficient, effective diameter and in certain instances, the average molecular weight.

For the simplest case of monodisperse particles, the field correlation is a single decaying exponential. If the polydispersity is not too great, the field autocorrelation function is nearly exponential. Two parameters that are frequently used to characterize particle distribution are the average decay rate and the polydispersity parameter.

The diffusion coefficient (D) is also related to the correlation function Cm(t) determined by the correlator by the following equation: $Cm(t) = A + B\ e^{-2DK2m(t)}$ where:

A, B=constants dependent on the physical details of the measurement

K=the scattering constant for the eye which is $4\pi/\lambda$ (sin θ/2) where λ is the wavelength and θ is the scattering angle.

t=the length of the predetermined time interval m=an integer whose range is the number of correlator channels Therefore, the values of the diffusion coefficient D and the constants A and B in the above equation can be determined, with the aid of computer, from the autocorrelation curve produced by the correlator 265 by using standard curve fitting and analysis techniques. The calculated diffusion coefficient, the average decay rate, the polydispersity parameters, the statistical uncertainties of each of these parameters and other calculated mathematical terms including the effective diameter and molecular weight, can be stored in the computer along with other patient data.

The apparatus shown in FIGS. 1 and 2 is used to perform a measurement as follows: with a patient sitting at the fundus camera, the operator sets up the device in the same way that the device would be set up during a normal ophthalmic procedure to take a fundus photograph. In order to measure various positions within the retina or choroid it may be necessary that the pupil be dilated using routinely available dilating drops as normally used during the course of a complete ophthalmic evaluation.

The illumination light of the fundus camera is used to focus the laser beam on the desired spot on the retina. The illumination beam is turned off when the measurement is made.

An infrared system may be used to aid in the maintenance of the light beam at the measurement site during the time the fundus camera illumination light is off.

In order to accurately compare measurements made from an individual with measurements made from the same individual at a later time or with measurements from a different individual, the compared measurements could be made from approximately the same position in the retina. Measurements obtained from other positions in the retina may give somewhat different results, which can provide additional information concerning the health of the patient.

Patients with dementia can demonstrate a slowing of the Brownian movement of the retinal proteins as compared to a patient without dementia.

At the present time, vascular endothelial growth factor inhibitors are injected into the vitreous cavity of patient's eyes to treat neovascular or "wet" age-related macular degeneration. Using the above system, preliminary results have demonstrated that the average decay constant, or Gamma, decreases immediately following injection. It appears that successful treatment resulting in the resolution of subretinal fluid and a decrease in leakage results in an increase in Gamma, and unsuccessful treatment does not, and that eyes receiving multiple injections of some of these types of drugs may exhibit lower measurements than the fellow, untreated eye which may have future negative consequences on the health of the eye.

Patients undergoing retinal or optic nerve stem cell surgery have been tested using this system. A measurement is made from the posterior pole of the retina the day before surgery, and the patient is re-measured at 3 months and 6 months postoperatively. Preliminary data indicates that though there may not be any visible changes by fundus photography or OCT in those patients with improved vision after the stem cell surgery, the postoperative diffusion coefficient is greater than the preoperative measurement. Those patients whom did not experience an improvement in vision after the stem cell surgery did not demonstrate a change in the diffusion coefficient postoperatively.

FIG. 7 illustrates a headset that can be modified with attachments for the incident fiber optic that provides the light, and the detection fiber optic that measures the back-scattered light, arranged vertically in front of the left eye. The two attachments can be connected to a rotating plate that may pivot 360 degrees so the attachments are arranged vertically, or horizontally. The rotating plate can be attached to another larger rotating face plate with a central attachment to the front of the headset such that it may pivot 360 degrees so that either the right or left eye may be tested.

FIG. 8 illustrates that when the face plate is rotated 180 degrees, the fiber connectors can be rotated from the patient's left eye to the right eye. The two connectors may be rotated in horizontal fashion as seen in FIG. 9. The rotation feature may also be utilized if testing of the other eye is desired. In the horizontal example, the outer fiber connector can remain in the same position whether the right or the left eye is being tested.

Figure 10:
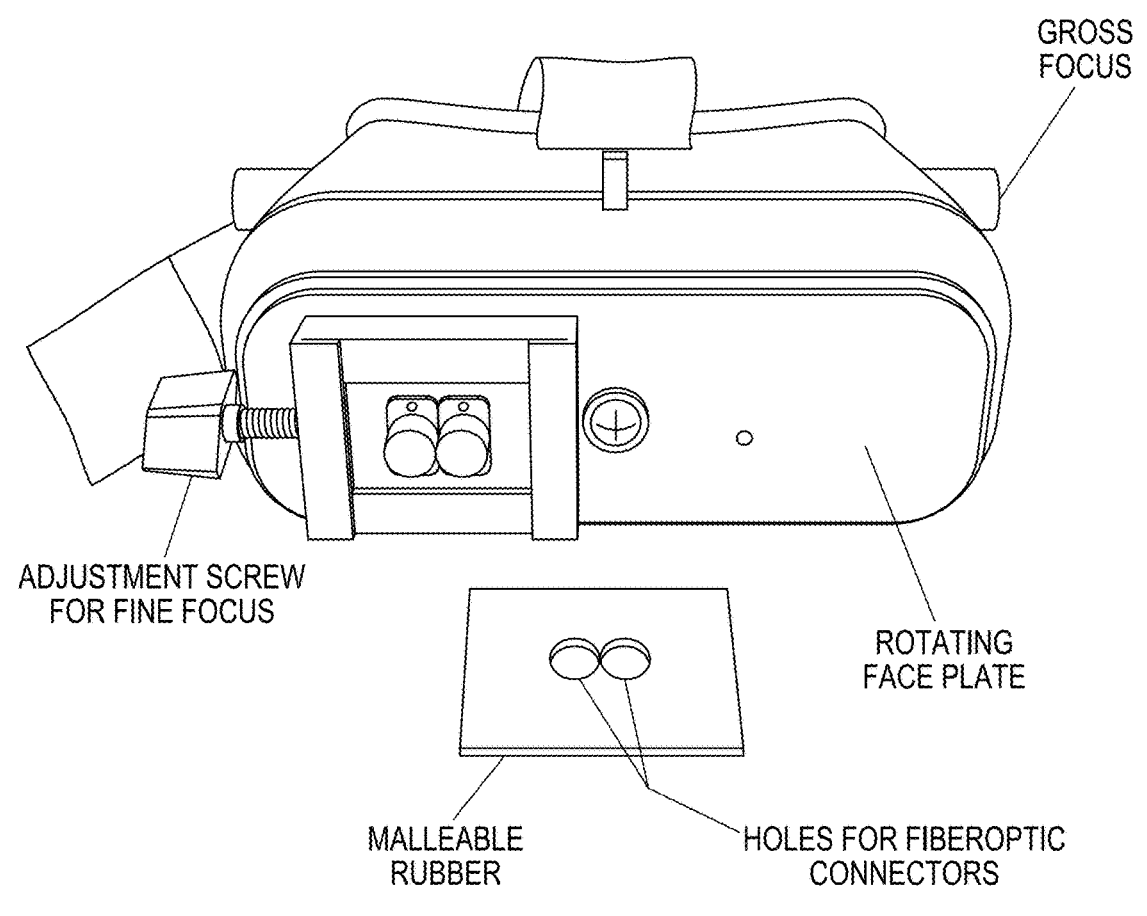
FIG. 10 illustrates goggles with an adjustment screw that can change the direction of the incident and detection fiber optics so that they can be focused on the same spot on the retina in accordance with the present disclosure.

FIG. 10 illustrates goggles with an adjustment screw that can change the direction of the incident and detection fiber optics so that they are focused on the same spot on the retina. In order to accommodate different faces, and eyes, the gross focus on the goggles may be used, followed by the fine focus. An automatic focusing arrangement may also be utilized. The two fiberoptic holders can be inserted in a rubber plate that allows the adjustment screw to change the incident angles into the eye so that the fiberoptics are pointing in the same direction.

Figure 11:
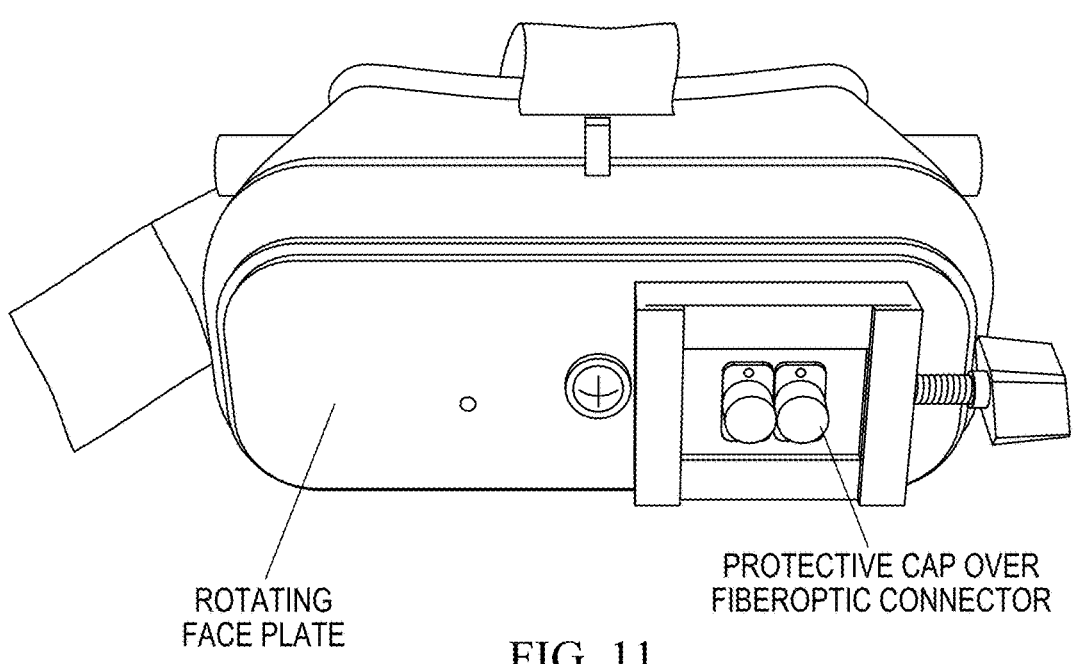
FIG. 11 illustrates the face plate can be rotated so that the opposite eye may be tested in accordance with the present disclosure.

FIG. 11 illustrates the face plate rotated so that the opposite eye may be tested. The position of the inner and outer fibers can remain the same regardless of which eye is being tested. A window may be added to the goggles so that the examiner may confirm the alignment of the incident and detection fiberoptics. Alternatively, the rotating face plate may be transparent.

Figure 12:
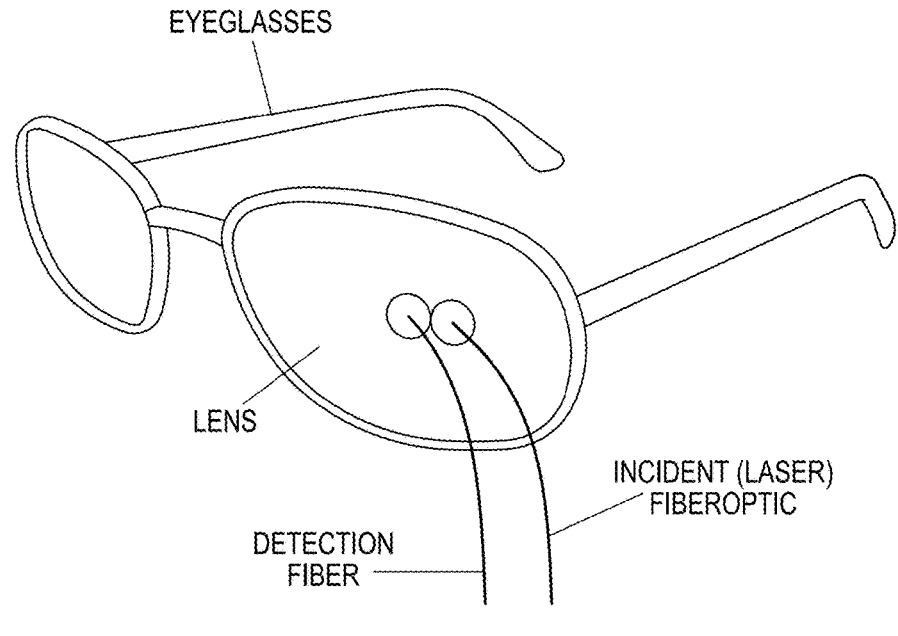
FIG. 12 illustrates the incident and the detection fiber optics can be directly mounted in the frame of a pair of eyeglasses.

FIG. 12 illustrates the incident and the detection fiberoptics can be directly mounted in the frame of a pair of eyeglasses. The illustration shows the fiberoptics mounted in front of the left eye but a second set of fiberoptics may also be mounted in front of the right eye. Alternatively, the fiberoptics in front of the left eye may be removed from the frame and inserted into the frame in front of the right eye. A mechanism to adjust the angles of the fiberoptic entry into the eye may be incorporated into the device. FIG. 12 also shows horizontal positioning of the fiberoptics but a rotation feature may be incorporated to change the position of the fiberoptics to vertical.

Figure 13:
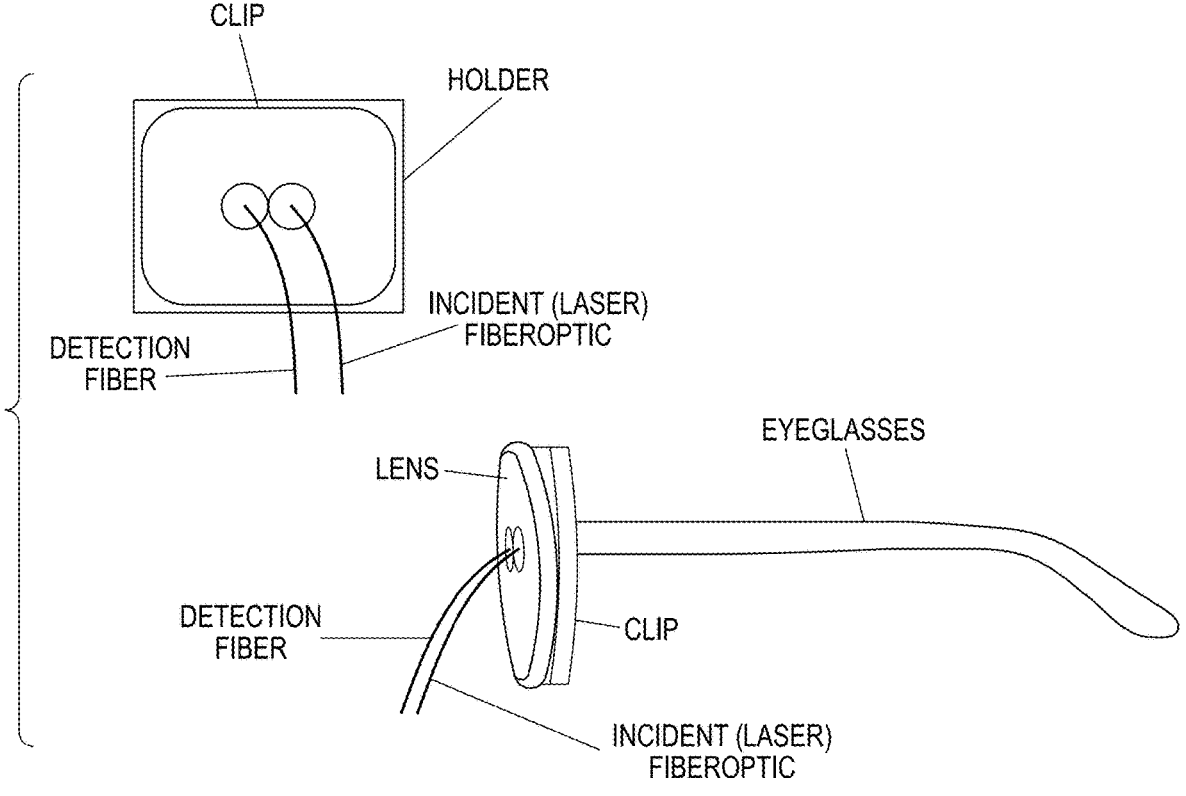
FIG. 13 illustrates the incident and the detection fiber optics can be mounted on a clip that may be attached to a patient's own eyeglasses.

FIG. 13 illustrates the incident and the detection fiberoptics mounted on a clip that may be attached to a patient's own eyeglasses. A mechanism to adjust the angles of the fiberoptic entry into the eye may be incorporated into the device. FIG. 13 also shows horizontal positioning of the fiberoptics, but a rotation feature may be incorporated to change the position of the fiberoptics to vertical.

Figure 14:
FIG. 14 illustrates that both fiberoptics, the incident and the detection fiberoptic, can be placed in front of either eye in accordance with the present disclosure.

FIG. 14 shows that both fiberoptics, the incident and the detection fiberoptic, can be placed in front of either eye. Both of the fibers can be located inside the beige tube. An adjustment mechanism can be provided to adjust the location of the fiberoptics entering the eye dependent on the location of the person's pupil. The rubber grommet shown in the drawing may not be necessarily in the right location for the light to enter the eye. Adjustment(s) may be needed to move the fiberoptics to the correct location. Both fiberoptics can be placed into a device that can clip onto a person's eyeglasses.

Figure 15:
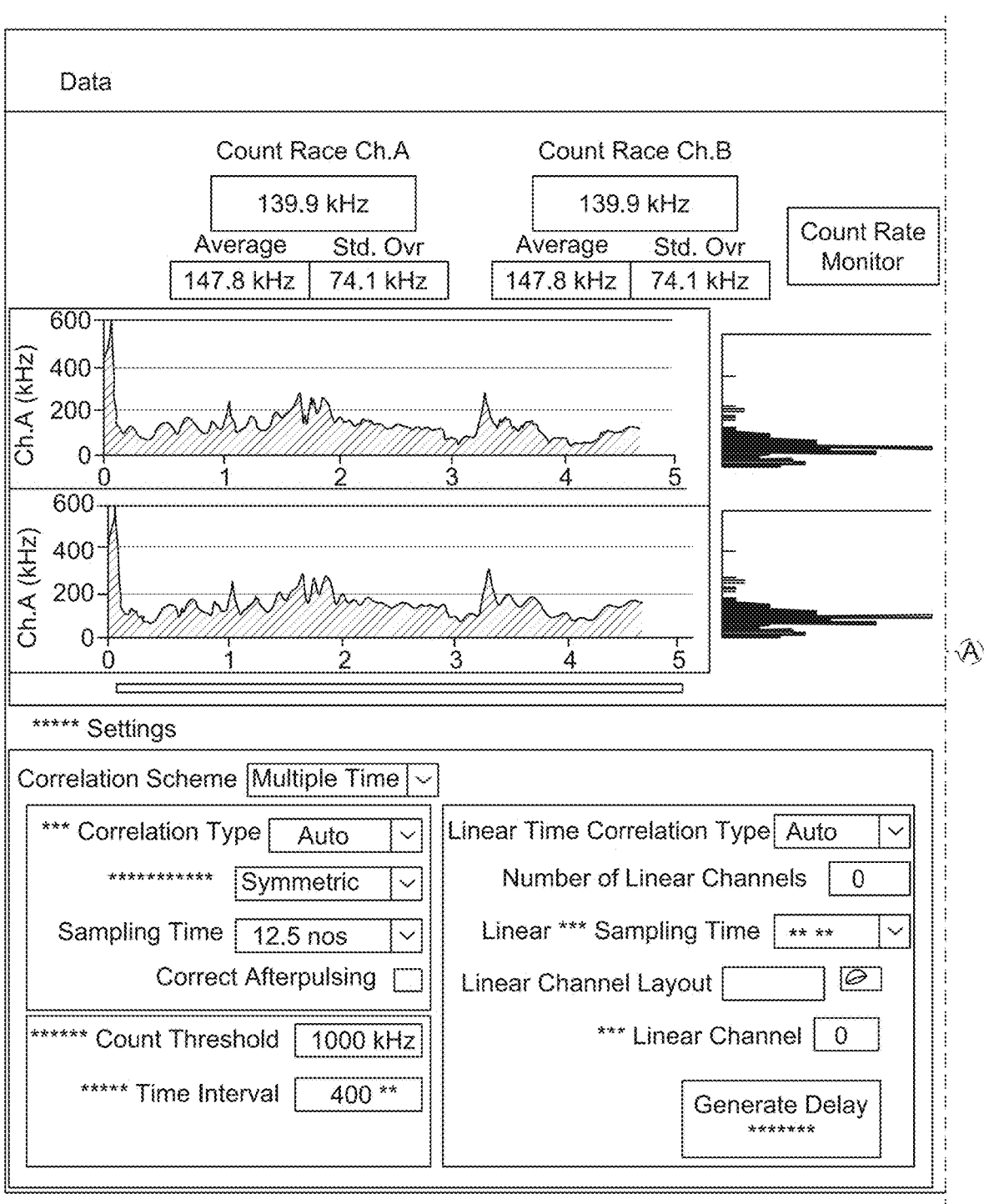
FIG. 15 is a non-limiting, example screenshot of a DLS measurement, showing the DLS measurement of a 62-year-old female diagnosed with Alzheimer's disease.
Figure 15:
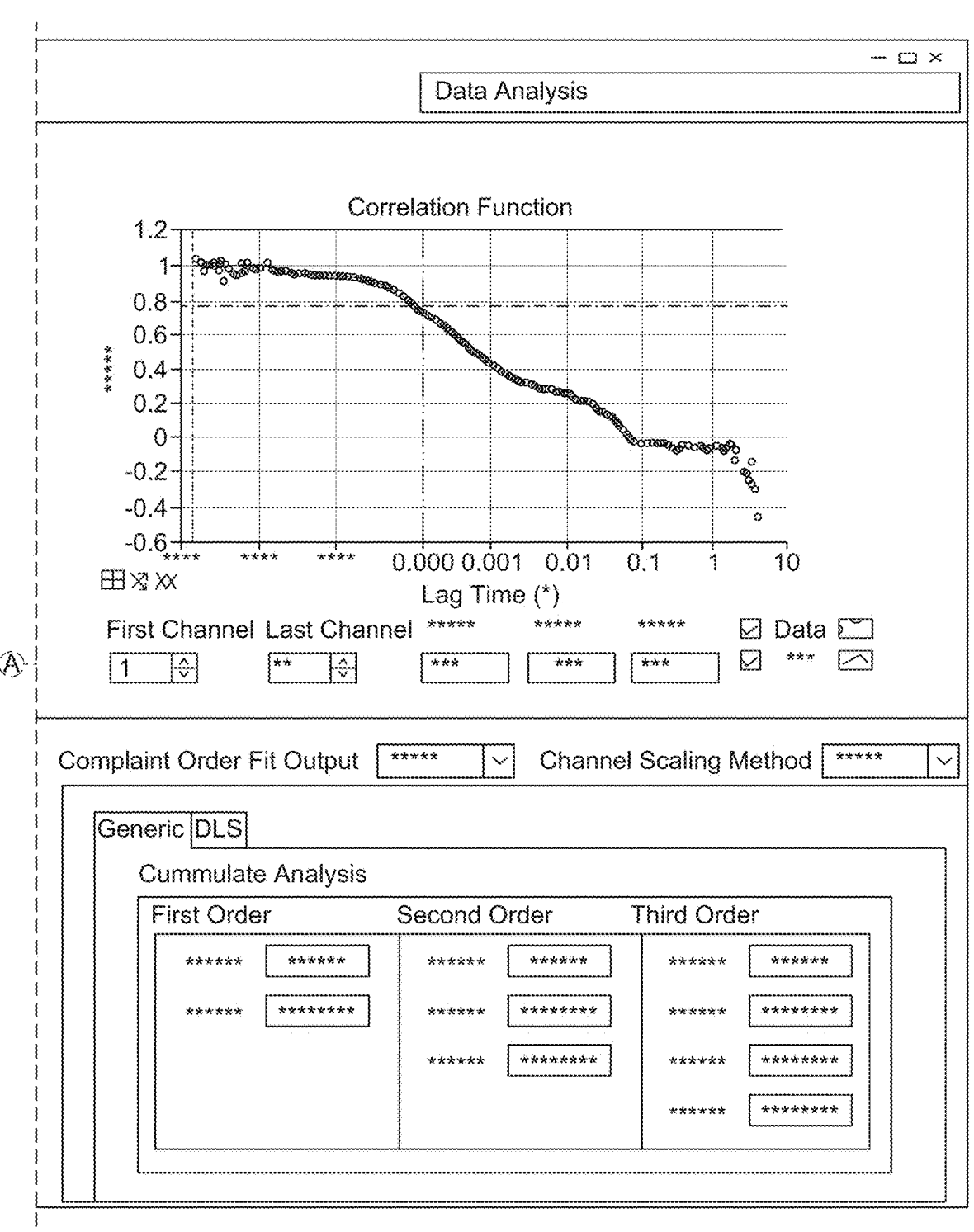
Figure 16:
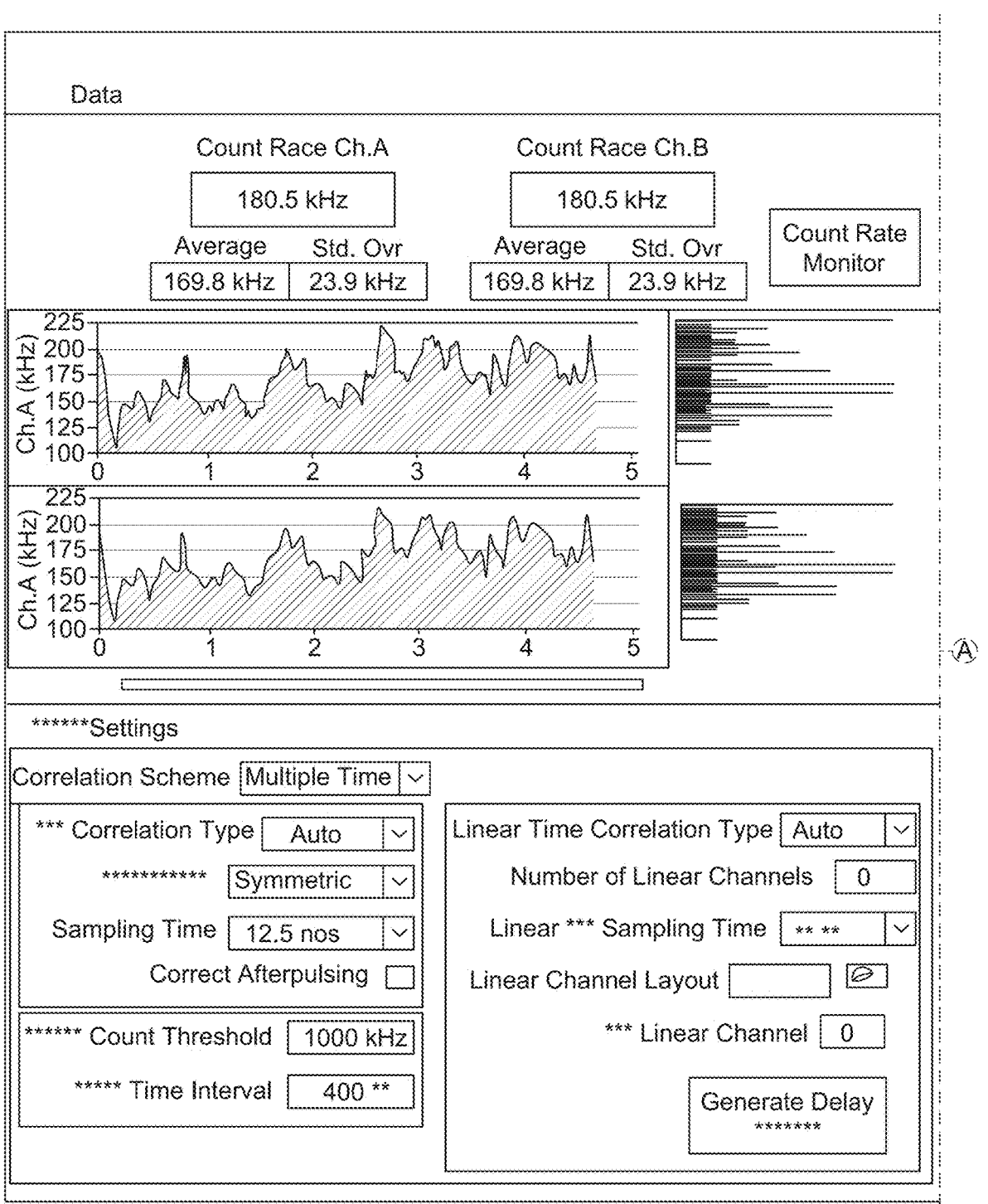
FIG. 16 is a non-limiting, example screenshot of a DLS measurement of an age-matched normal control patient.
Figure 16:
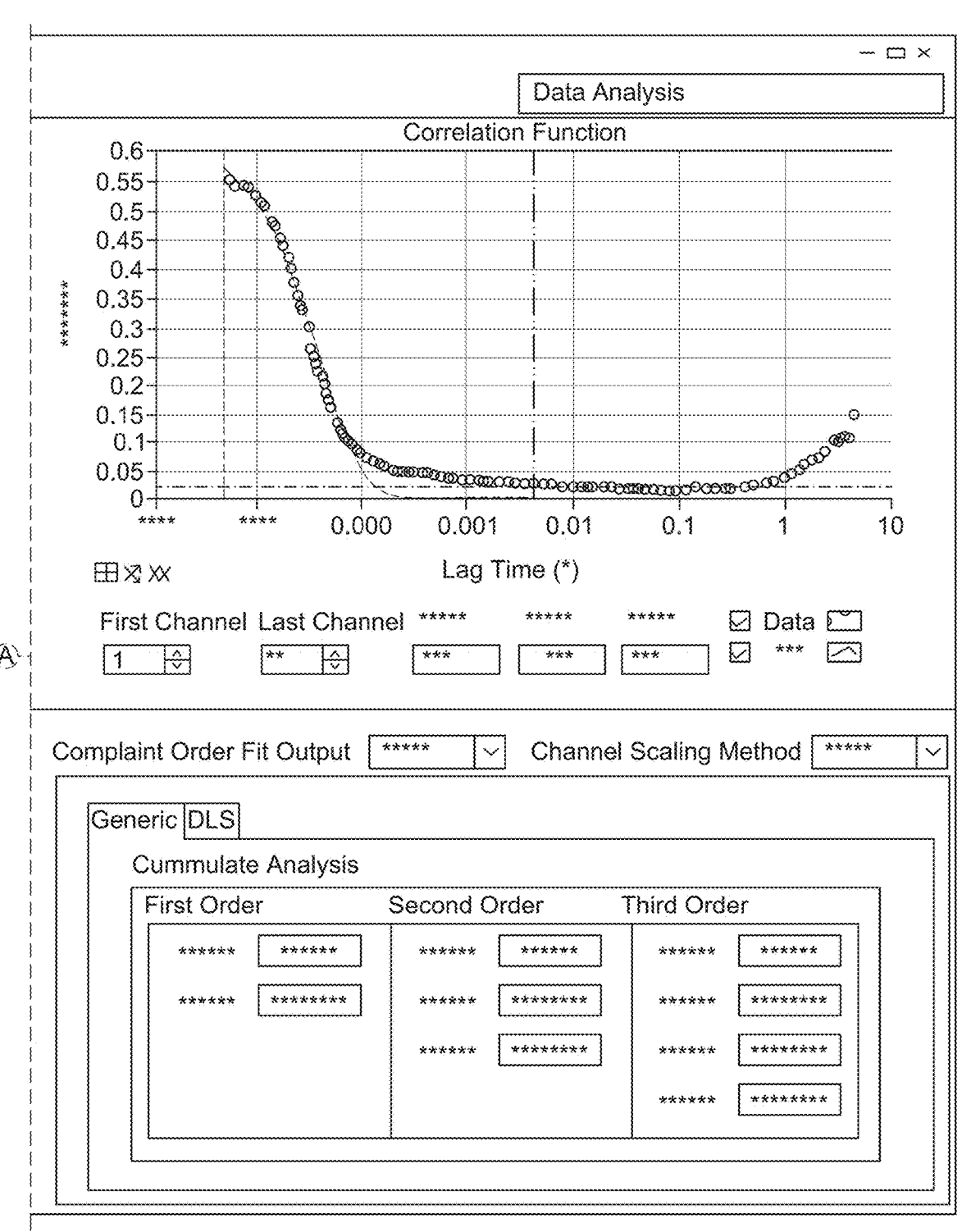

FIG. 15 is a non-limiting, example screenshot of a DLS measurement of a 62-year-old female diagnosed with Alzheimer's disease; whereas FIG. 16 is a non-limiting, example screenshot of a DLS measurement of an age-matched normal control patient. Alzheimer's measurements consistently begin above 0.6 $g^{2(1)-1}$ and exhibit flattening of the initial line, as opposed to the curve seen in non-Alzheimer's patients (FIG. 16).

The novel system and method measure the correlation between the light at one moment in time to subsequent moments in time at the same spot of the patient's retina. Where the intensity is approximately the same, and there is minimal fluctuation, this can mean that the scatterer is a large, or slow-moving molecule, because there was minimal fluctuation. When this is seen, it allows the user to diagnose Alzheimer's for the patient. A normal (i.e. no dementia/Alzheimer) patient should have a more rapid fluctuation in the light intensity. The novel system and method also select proper sampling times and measurement duration that are chosen to differentiate between patients with cognitive impairment and dementia and those without these findings. The system and method are involved and concerned with the change in the correlation of the light over designated time interval/particular sampling time.

Amyloid is a late finding in Alzheimer's. It has been demonstrated that the removal of the amyloid has no impact on the patient's clinical course. While the presence of amyloid has been implicated in inherited Alzheimer's disease, other factors, such as inflammation and blood vessel health, which can also be reflected in the measurements taken by the novel system and method can also lead to Alzheimer's.

The instant method does not measure an abnormal protein, but rather is measuring a normal, existing protein whose movement within the retina is slowing. The disclosed novel system and method can be used to detect a change in the Brownian movement of a normal protein, not a new protein, nor amyloid. Also, as noted above, with the use of the disclosed system and method, measurements are taken from the same spot of the patient's eye.

The disclosed method makes a measurement from a normal looking retina, which allows the system and method to detect Alzheimer's much, much, earlier as compared to current systems/methods.

The novel disclosed system and method also use relatively short and longer sampling times, which can be based on whether a small/fast molecule is present or a large/slow molecule is present, which can play a role in whether anything will be seen by the user. A correct sample time is needed in order to determine a fluctuation in light intensity.

Also disclosed is a novel method for using the DLS device to assess the efficacy of therapeutic agents and for the development of new therapeutic agents in a relatively shorter amount of time. In order to determine the efficacy of a new therapeutic agent, a baseline DLS measurement can be made from a patient. The therapeutic agent would then be started or otherwise provided to or for the patient, and longitudinal DLS measurements made over time to determine whether the DLS measurement worsened over time (i.e. as compared to the baseline DLS measurement), which is defined as a slowing of the proteins. A worsening of the DLS measurement is expected in an untreated dementia patient over time. Stability or improvement in the DLS measurement, (the proteins would not slow down, or the Brownian movement would not change, or even increase) would demonstrate drug efficacy.

With the novel method, drug efficacy can be determined much earlier than the present method of waiting for the patient to decline cognitively over time, which can take years, or another endpoint. The determination of efficacy may be shortened from years, to months. Since drug studies would be shorter, they would be much less expensive to conduct leading to the development and testing of more new therapeutic agents.

All locations, sizes, shapes, measurements, amounts, angles, voltages, frequencies, component or part locations, configurations, temperatures, weights, dimensions, values, time periods, percentages, materials, orientations, etc. discussed above or shown in the drawings are merely by way of example and are not considered limiting and other locations, sizes, shapes, measurements, amounts, angles, voltages, frequencies, component or part locations, configurations, temperatures, weights, dimensions, values, time periods, percentages, materials, orientations etc. can be chosen and used and all are considered within the scope of the invention.

Dimensions of certain parts as shown in the drawings may have been modified and/or exaggerated for the purpose of clarity of illustration and are not considered limiting.

Changes and modifications within the spirit and scope of the invention will be apparent to those skilled in ophthalmology. It is expected that advancements in electronics will simplify the design of this system. The diffusion coefficient can be replaced by another measure such as the decay constant. The essential point is that variations in the intensity of the back-scattered light are the basis of the measurement. That measurement may then be utilized to obtain derivatives. The form in which those variations are presented is mainly a matter of individual preference. Such obvious modifications and changes are intended to be covered by the appended claims.

Unless feature(s), part(s), component(s), characteristic(s) or function(s) described in the specification or shown in the drawings for a claim element, claim step or claim term specifically appear in the claim with the claim element, claim step or claim term, then the inventor does not considered such feature(s), part(s), component(s), characteristic(s) or function(s) to be included for the claim element, claim step or claim term in the claim for examination purposes and when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the invention has been described and disclosed in certain terms and has disclosed certain embodiments or modifications, persons skilled in the art who have acquainted themselves with the invention, will appreciate that it is not necessarily limited by such terms, nor to the specific embodiments and modification disclosed herein. Thus, a wide variety of alternatives, suggested by the teachings herein, can be practiced without departing from the spirit of the invention, and rights to such alternatives are particularly reserved and considered within the scope of the invention.

What is claimed is:

1. An optical apparatus adapted for use with a fundus camera, OCT machine or similar ophthalmic device in connection with measuring Brownian movement of particles in connection with detecting dementia or retina conditions for a patient, comprising:

a body member;

a detection optical fiber secured to or within the body member; an incident optical fiber secured to or within the body member;

a laser light source that produces monochromatic light at a single particular wavelength and which passes the monochromatic light through the incident optical fiber;

a linear positioner secured to the body member for varying a measurement spot on a subject's or patient's retina;

a plurality of folding mirrors secured to the body member; and a beam splitter mirror positioned adjacent to the subject's or patient's face during use;

wherein the plurality of folding mirrors and beam splitter mirror place an incident beam into a frame of an image of the subject's or patient's retina created by a fundus camera, OCT machine or similar ophthalmic device;

wherein the detection optical fiber sensitive to transmit the single particular wavelength.

2. The optical apparatus of claim 1 wherein the body member defining a termination and the optical fiber is mounted within the termination.

3. The optical apparatus of claim 1 further comprising a plate member adapted to be rotatable with respect to the fundus camera, OCT machine or similar ophthalmic device for changing a beam scan angle.

4. The optical apparatus of claim 3 wherein the body member is secured to the plate member.

5. The optical apparatus of claim 3 further comprising a beam splitter holder secured to the plate member and adapted for holding the beam splitter mirror.

6. The optical apparatus of claim 1 wherein the incident optical fiber is a single mode optical fiber.

7. The optical apparatus of claim 1 wherein the detection optical fiber is a single mode optical fiber.

8. The optical apparatus of claim 1 wherein the monochromatic light generated by the laser light source is provided on the retina in conjunction with measuring Brownian movement of particles for a patient.

9. An optical apparatus adapted for use with a fundus camera, OCT machine or similar ophthalmic device, comprising:

a body member;

a detection optical fiber secured to or within the body member; an incident optical fiber secured to or within the body member;

a laser light source that passes light through the incident optical fiber;

a linear positioner secured to the body member for varying a measurement spot on a subject's or patient's retina;

a plurality of folding mirrors secured to the body member; and a beam splitter mirror positioned adjacent to the subject's or patient's face during use;

wherein the plurality of folding mirrors and beam splitter mirror place an incident beam into a frame of an image of the subject's or patient's retina created by a fundus camera, OCT machine or similar ophthalmic device; and wherein the detection optical fiber is attached to the linear positioner such that incident light and detection light are simultaneously varied by a same amount when the linear positioner is used to vary the measurement spot.

10. The optical apparatus of claim 9 wherein the body member defining a termination and the optical fiber is mounted within the termination.

11. The optical apparatus of claim 9 further comprising a plate member adapted to be rotatable with respect to the fundus camera, OCT machine or similar ophthalmic device for changing a beam scan angle.

12. The optical apparatus of claim 11 wherein the body member is secured to the plate member.

13. The optical apparatus of claim 11 further comprising a beam splitter holder secured to the plate member and adapted for holding the beam splitter mirror.

14. An optical apparatus adapted for use with a fundus camera, OCT machine or similar ophthalmic device, comprising:

a body member;

a detection optical fiber secured to or within the body member; an incident optical fiber secured to or within the body member;

a laser light source that passes light through the incident optical fiber;

a linear positioner secured to the body member for varying a measurement spot on a subject's or patient's retina;

a plurality of folding mirrors secured to the body member; and a beam splitter mirror positioned adjacent to the subject's or patient's face during use;

wherein the plurality of folding mirrors and beam splitter mirror place an incident beam into a frame of an image of the subject's or patient's retina created by a fundus camera, OCT machine or similar ophthalmic device; and further comprising a single photon counting module for detecting a light output from the detection optical fiber.

15. The optical apparatus of claim 14 wherein the body member defining a termination and the optical fiber is mounted within the termination.

16. The optical apparatus of claim 14 further comprising a plate member adapted to be rotatable with respect to the fundus camera, OCT machine or similar ophthalmic device for changing a beam scan angle.

17. The optical apparatus of claim 16 wherein the body member is secured to the plate member.

18. The optical apparatus of claim 16 further comprising a beam splitter holder secured to the plate member and adapted for holding the beam splitter mirror.

* * * * *